US012370147B2

(12) United States Patent
Buser et al.

(10) Patent No.: US 12,370,147 B2
(45) Date of Patent: Jul. 29, 2025

(54) COATABLE CORE FOR A MODIFIED RELEASE DRUG FORMULATION

(71) Applicant: Tillotts Pharma AG, Rheinfelden (CH)

(72) Inventors: Thomas Buser, Nuglar (CH); Yalcin Cetinkaya-Coskun, Rheinfelden (CH); Roberto Carlos Bravo González, Rheinfelden (CH)

(73) Assignee: Tillotts Pharma AG, Rheinfelden (CH)

( * ) Notice: Subject to any disclaimer, the term of this patent is extended or adjusted under 35 U.S.C. 154(b) by 712 days.

(21) Appl. No.: 17/309,557

(22) PCT Filed: Dec. 5, 2019

(86) PCT No.: PCT/EP2019/083911
§ 371 (c)(1),
(2) Date: Jun. 4, 2021

(87) PCT Pub. No.: WO2020/115256
PCT Pub. Date: Jun. 11, 2020

(65) Prior Publication Data
US 2022/0016040 A1    Jan. 20, 2022

(30) Foreign Application Priority Data

Dec. 7, 2018  (EP) .................................. 18211145

(51) Int. Cl.
*A61K 9/20*     (2006.01)
*A61K 9/28*     (2006.01)
*A61K 31/196*   (2006.01)

(52) U.S. Cl.
CPC .......... *A61K 9/2893* (2013.01); *A61K 9/2054* (2013.01); *A61K 31/196* (2013.01)

(58) Field of Classification Search
CPC .......... A61K 9/14; A61K 9/20; A61K 9/2004; A61K 9/2009; A61K 9/2095
See application file for complete search history.

(56) References Cited

U.S. PATENT DOCUMENTS

| 4,539,198 A * | 9/1985 | Powell ................. A61K 9/2004 514/960 |
| 5,422,121 A | 6/1995 | Lehmann et al. |
| 2008/0200482 A1 | 8/2008 | Petereit et al. |
| 2012/0100214 A1* | 4/2012 | Segura ................. A61K 9/2886 424/475 |
| 2015/0374632 A1* | 12/2015 | Ryu ..................... A61K 31/606 424/475 |
| 2016/0250232 A1 | 9/2016 | Varum et al. |

FOREIGN PATENT DOCUMENTS

| CN | 105555260 | 5/2016 |
| EP | 0 343 993 | 11/1989 |
| EP | 0 502 032 | 9/1992 |
| GB | 2367002 | 3/2002 |
| JP | S56-14098 | 2/1981 |
| JP | 2015-515964 | 6/2015 |
| JP | 2015-515965 | 6/2015 |
| JP | 2016-513724 | 5/2016 |
| JP | 2016-535030 | 11/2016 |
| KR | 10-2014-0001236 | 1/2014 |
| KR | 10-2015-0118160 | 10/2015 |
| KR | 10-2016-0077040 | 7/2016 |
| WO | 91/07949 | 6/1991 |
| WO | 96/36321 | 11/1996 |
| WO | 99/21536 | 5/1999 |
| WO | 99/25325 | 5/1999 |
| WO | 01/76562 | 10/2001 |
| WO | 03/068196 | 8/2003 |
| WO | 2004/052339 | 6/2004 |
| WO | 2008/135090 | 11/2008 |
| WO | 2012/075455 | 6/2012 |
| WO | 2013/164315 | 11/2013 |
| WO | 2013/164316 | 11/2013 |
| WO | 2014/129568 | 8/2014 |
| WO | 2014/143935 | 9/2014 |

(Continued)

OTHER PUBLICATIONS

Yamamura et al, Effects of automated external lubrication on tablet properties and the stability of eprazinone hydrochloride; International Journal of Pharmaceutics, 370, 2009, 1-7 (Year: 2009).*
Katsuio Kataoka, "Cases Experienced to be Noted in relation to Tableting Process", Pharmaceutics, vol. 68, No. 6, 2008, pp. 435-440, with English translation.
Oneda et al. "Development of External Lubrication System for Tableting and its Application a Wide Field of Industry", Japan Society of Pharmaceutical Machinery and Engineering., vol. 18, No. 4, 2009, pp. 5-17, with English translation.
Japanese Office Action dated Jul. 15, 2022, in Japanese Patent Application No. 2021-532422, with English translation, 12 pages.
International Search Report issued Feb. 2, 2020 in PCT/EP2019/083911.
Written Opinion issued Feb. 2, 2020 in PCT/EP2019/083911.
Akhgari et al., "Permeability and swelling studies on free films containing inulin in combination with different polymethacrylates aimed for colonic drug delivery", European Journal of Pharmaceutical Sciences, vol. 28, Mar. 2006, pp. 307-314.

(Continued)

*Primary Examiner* — Micah Paul Young
(74) *Attorney, Agent, or Firm* — Grüneberg and Myers PLLC

(57) ABSTRACT

A method produces a coatable core for a modified release drug formulation for oral administration. The coatable core has a high drug load of at least 70 wt % based on the total weight of the coatable core. The method involves the steps of granulating a composition containing a drug and at least one binder to form granules; blending the granules with a pharmacologically acceptable disintegrant and optionally, one or more additional pharmacologically acceptable excipients, to form a compression blend, wherein the disintegrant is present in an amount from about 0.5 wt % to about 5 wt %, based on the total weight of the coatable core; and compressing the compression blend using an external lubrication compression method to form a coatable core.

12 Claims, 3 Drawing Sheets

(56) References Cited

FOREIGN PATENT DOCUMENTS

WO      2015/062640      5/2015

OTHER PUBLICATIONS

Chinese Office Action dated Jul. 1, 2022, in Chinese Patent Application No. 201980081083.2, with English translation, 11 pages.
Chinese Office Action dated Jan. 18, 2023, in Chinese Patent Application No. 201980081083.2, with English translation, 13 pages.
Japanese Office Action dated Jan. 6, 2023, in Japanese Patent Application No. 2021-532422, with English translation, 8 pages.
Japanese Decision to Grant a Patent dated Jun. 27, 2023, in Japanese Patent Application No. 2021-532422, with English translation, 6 pages.
Kondo et al., "Effect of the External Lubrication Method for a Rotary Tablet Press on the Adhesion of the Film Coating Layer", Chem Pharm Bull, vol. 65, No. 9, 2017, pp. 848-853.
Milojevic et al., "Amylose as a coating for drug delivery to the colon: Preparation and in vitro evaluation using 5-aminosalicylic acid pellets", Journal of Controlled Release, vol. 38, 1996, pp. 75-84.
Chinese Office Action dated Sep. 13, 2023, in Chinese Application No. 201980081083.2, with English translation, 19 pages.
Canada First Examination Report received for Canadian Patent Application No. 3,122,031, mailed on Mar. 13, 2024, 7 pages.
Chinese Decision of Rejection received for Chinese Patent Application No. 201980081083.2, mailed on Feb. 9, 2024, 19 pages with English translation.
Communication Pursuant to Article 94(3) EPC received for European Patent Application No. 18211145.0, mailed on Mar. 15, 2024, 4 pages.
Japanese First Examination report received for Japanese Patent Application No. 2023-093381, mailed on May 31, 2024, 9 pages with English translation.
Korean First Examination report received for Korean Patent Application No. 10-2021-7020597, mailed on Apr. 5, 2024, 24 pages with English translation.
Taiwanese First Examination report received for Taiwanese Patent Application No. 108144377, mailed on Jul. 4, 2023, 21 pages with English translation.
Taiwanese Grant Request received for Taiwanese Patent Application No. 108144377, mailed on Jun. 21, 2024, 10 pages with English translation.
Office Action issued in Korean Patent Application No. 10-2021-7020597 on Jan. 20, 2025, 12 pages (with English translation).
Office Action issued in Japanese Patent Application No. 2023-093381 on Jan. 17, 2025, 5 pages (with English translation).

\* cited by examiner

COATABLE CORE FOR A MODIFIED RELEASE DRUG FORMULATION

CROSS-REFERENCE TO RELATED APPLICATIONS

This application is the National Stage entry under § 371 of International Application No. PCT/EP2019/083911, filed on Dec. 5, 2019, and which claims the benefit of priority to European Application No. 18211145.0, filed on Dec. 7, 2018. The content of each of these applications is hereby incorporated by reference in its entirety.

BACKGROUND OF THE INVENTION

Field of the Invention

The present invention relates to a method of producing a coatable core for an oral drug formulation, and preferably for a modified release drug formulation for oral administration and a delayed release drug formulation produced therefrom. In particular, it relates to a coatable core for a delayed release formulation for a drug for delivering to the intestine. The coatable core of the present invention could also be used in drug formulations for delivering a drug to the stomach or small intestine.

Description of Related Art

The targeting of drugs to the intestine is well known and has been known for over one hundred years. Commonly, the target of the drugs is the small intestine although the colon can be utilised as a means of achieving local therapy or systemic treatment. The requirements for the coatings on the drugs are different depending on the target site. In order to reach the colon, it is necessary for the drugs to pass through the small intestine, and therefore it is a requirement that a delayed release coating intended to release the drug in the colon does not release the drug in the small intestine.

Coated products for release in the small intestine commonly use polymer coatings which dissolve or disintegrate in a pH dependent manner. In the low pH environment of the stomach, the polymer coating is insoluble. However, on reaching the small intestine, the pH rises to 5 and above and the polymeric coating dissolves or disintegrates. A commonly used coating is one containing ionizable carboxylic groups. At higher pH levels, the carboxylic groups ionize, allowing the polymer coatings to disintegrate or dissolve. Common polymers of this type which are used include Eudragit® L and Eudragit® S.

Various methods of improving the release in the small intestine by ensuring an earlier release of the drug are known. US2008/0200482 is one of a number of references which discloses partially neutralizing the carboxylic groups in order to reduce the pH at which disintegration occurs. WO2008/135090 discloses a tablet with an inner coat of partially neutralized material and an outer coat with less or no neutralization. This is said to result in disintegration at an earlier time point when transferred from the stomach.

Release of drugs in the colon typically requires an alternative approach. The colon is susceptible to a number of disease states, including inflammatory bowel disease, irritable bowel syndrome, constipation, diarrhoea, infection and carcinoma. In such conditions, drug targeting to the colon would maximise the therapeutic effectiveness of the treatment. The colon can also be utilised as a portal for the entry of drugs into the systemic circulation. Various formulations have been developed for colonic drug delivery, including pro-drugs as well as formulated dosage forms, with the latter being more popular since the concept once proved can be applied to other drugs.

The high bacterial population of the colon has also been exploited in developing colonic drug delivery dosage forms through the use, as digestible carrier materials, of naturally occurring polysaccharides that constitute substrates for the numerous enzymes produced by the resident colonic bacteria. These materials are able to pass through the upper gastrointestinal regions intact but are digested upon entry into the colon. Examples include starch, amylopectin, amylose, pectin, chitosan, galactomannan and guar gum.

One major attraction of using polysaccharides in this bacterial enzyme approach to colonic drug delivery is that materials used are of food grade and so would be safe for use in humans. They are usually applied as coatings or incorporated in the core material as a matrix carrier, and their digestion on entry into the colon by the colonic bacterial enzymes leads to the release of the drug load. An example of such a formulation, which employs an amylose coating, is disclosed in EP0343993A (BTG International Limited).

A major limitation with these naturally occurring materials, however, is that they swell excessively in aqueous media leading to leaching of the drug load in the upper gastrointestinal regions. To circumvent this problem, the naturally occurring materials have been utilised in a mixture with various impermeable materials.

EP0502032A (British Technology Group Ltd) teaches the use of an outer coating comprising a film-forming cellulose or acrylate polymer material and amorphous amylose for a tablet comprising an active compound. The polymer material used is a pH independent release polymer material.

An article in Journal of Controlled Release (Milojevic et al; 38; (1996); 75-84) reports the results of investigations concerning the incorporation of a range of insoluble polymers into an amylose coating in order to control amylose swelling. A range of cellulose and acrylate based co-polymers are assessed, and a commercially available ethyl cellulose (Ethocel®) is found to control the swelling most effectively. A pH dependent soluble coating of Eudragit® L100 is employed but only in a multi-layer system comprising a bioactive coated with an inner coating of amylose and then an outer coating of Eudragit® L100.

A further amylose-based coating composition is disclosed in WO99/21536A (BTG International Limited). The coating composition comprises a mixture of amylose and a water-insoluble pH independent film-forming polymer which is formed from a water-insoluble cellulosic or acrylate polymer material.

WO99/25325A (BTG International Limited) also discloses a delayed release coating comprising amylose and (preferably) ethyl cellulose or alternatively an insoluble acrylate polymer. The coating composition also includes a plasticiser and the method finds particular application in the preparation of dosage forms comprising active materials that are unstable at temperatures in excess of 60° C., as the composition is formed at lower temperatures than this.

WO03/068196A (Alizyme Therapeutics Ltd) discloses a specific delayed release coating for the bioactive prednisolone sodium metasulphobenzoate comprising glassy amylose, ethyl cellulose and dibutyl sebacate.

The use of polysaccharides other than amorphous amylose in a delayed release coating is disclosed in GB2367002 (British Sugar PLC). Examples include guar gum, karaya gum, gum tragacanth and xanthan gum. Microparticles of these polysaccharides are dispersed in a water-insoluble film-forming polymer matrix formed for example from a cellulose derivative, an acrylic polymer or a lignin.

WO01/76562A (Tampereen Patenttitoimisto Oy) discloses a peroral pharmaceutical formulation containing a drug and a chitosan (a polysaccharide obtained from chitin) for controlling its release. The drug and the chitosan are mixed into a homogeneous mechanical powder mixture which is granulated and then optionally tabletised. The granulation may be performed with an enteric polymer (such as a copolymer of methacrylic acid) or the granules may be provided with a porous enteric coating.

WO2004/052339A (Salvona LLC) discloses a pH dependent drug release system which is a free-flowing powder of solid hydrophobic nano-spheres comprising a drug encapsulated in a pH-sensitive micro-sphere. The nano-spheres are formed from the drug in combination with a wax material, and the pH-sensitive micro-sphere formed from a pH-sensitive polymer (such as a Eudragit® polymer) in combination with a water-sensitive material such as a polysaccharide.

An article in the European Journal of Pharmaceutical Sciences (Akhgari et al; 28; March 2006; 307-314) reports the results of investigations into the use of certain polymethacrylate polymers to, inter alia, control the swelling of inulin. The polymethacrylate polymers tested were Eudragit® RS; Eudragit® RL; 1:1 mixtures of Eudragit® RS and Eudragit® RL; Eudragit® FS; and 1:1 mixtures of Eudragit® RS and Eudragit® S.

U.S. Pat. No. 5,422,121 (Röhm GmbH) discloses an oral dosage form having a core containing at least one active ingredient enclosed within a shell material which comprises a polysaccharide that decomposes in the colon in admixture with a film-forming polymer. The ratio by weight of polysaccharide to film-forming polymer is from 1:2 to 5:1, preferably from 1:1 to 4:1. Premature diffusion of the active ingredient from the core can be suppressed using a gastric resistant isolating layer. The reference exemplifies inter alia tablets having an inner isolating layer of Eudragit® L30D with an outer layer comprising Eudragit® L30D and guar gum (Example 2).

WO96/36321A discloses an oral dosage form comprising a core containing bisacodyl, and an enteric polymer coating for the core, the coating comprising at least one inner coating layer and an outer coating layer. The or each of the inner coating layer(s) is an enteric polymer that begins to dissolve in an aqueous medium at a pH of from about 5 to about 6.3, and the outer coating layer is an enteric polymer that begins to dissolve in an aqueous medium at a pH of from about 6.8 to about 7.2. The enteric polymer coating materials for the inner layer(s) are selected from the group consisting of cellulose acetate phthalate; cellulose acetate trimellitate; hydroxypropyl methylcellulose phthalate; hydroxypropyl methylcellulose acetate succinate; polyvinyl acetate phthalate; poly(methacrylic acid, methyl methacrylate) 1:1; poly (methacrylic acid, ethyl acrylate) 1:1; and compatible mixtures thereof.

WO2013/164315A discloses a colonic drug delivery formulation comprising a core comprising a drug and a coating comprising an inner layer and an outer layer. A mixture of a pH dependent film-forming polymeric material and a polysaccharide such as starch is used as the outer layer and the inner layer is soluble in intestinal fluid or gastrointestinal fluid. The reference exemplifies inter alia tablet cores containing 1200 mg of 5-aminosalicyclic acid (5-ASA, also known as mesalamine or mesalazine) as the active compound. These tablet cores are prepared by wet granulation followed by fluid bed drying, blending and compression.

In a typical tablet compression process, a tableting or compression blend is introduced into a die where it is compressed into a tablet by two punches that fit the top and the bottom of the die. Compression of a tableting blend into tablets generally requires lubrication. Lubricants reduce friction between the particles or granules of the tableting blend with the filling unit and with the surfaces of the punches and dies during compression. Lubricants also reduce friction and between the surface of the tablet cores and the surfaces of the punches and dies during ejection. The presence of a lubricant reduces ejection force, reduces wear on the punches and dies of the tableting machine, and helps to ensure that the tablet does not stick to the die and is cleanly ejected from the tableting machine without cracking or breaking. Typically, lubricants are added to the tableting blend itself shortly before tableting. This is known as internal lubrication. The lubricant particles form a boundary layer on the particles or granules of the tableting blend. The presence of a lubricant in the tableting blend can improve the flowability of the blend by reducing inter-particulate friction. The 1200 mg tablet cores exemplified in WO2013/164315A contain 0.5 wt % of magnesium stearate as the internal lubricant. It has been identified during pilot plant production of delayed release drug formulations such as those disclosed in WO2013/164315A, and particularly for tablet cores greater than 1200 mg, that an amount of 0.5 wt % lubricant per tablet is, in certain circumstances, insufficient for adequate lubrication of the tableting machine. This is illustrated by an ejection force exceeding the limit set for the tableting machine.

However, increasing the amount of internal lubricant can result in an undesirable decrease in tablet hardness and increase in tablet friability, as well as a tendency for capping to occur. 'Capping' is a term used to describe when the upper or lower segment of a tablet separates horizontally, either partially or completely, from the main body of a tablet and comes off as a cap. This typically occurs during ejection of a tablet from a tableting machine, but can also occur subsequent handling. High levels of internal lubricant can also lead to prolonged disintegration time of the tablet cores as well as a risk of decreased dissolution due to the presence of hydrophobic boundary layers surrounding the particles of the tableting blend as well as hydrophobic bridges that form in the final compressed tablets. There is also the potential of stability problems on storage due to incompatibility of certain active pharmaceutical ingredients (API) with hydrophobic lubricants. It would therefore be desirable to provide an improved method for producing a coatable core having a high drug load. The coatable core must have a low friability, high hardness and must be capable of delivering a rapid disintegration time and fast drug release.

A further problem with existing delayed release formulations for the delivery of drugs such as 5-ASA, is that it is often necessary for patients to take multiple tablets to make up the required daily dose of the drug. It would therefore be further desirable to provide a modified release drug formulation for oral administration which has a coatable core having a high dose strength and minimal overall size, as this would allow for reduced dosing frequency and improve patient compliance.

SUMMARY OF THE INVENTION

In accordance with a first aspect of the present invention, there is provided a method of producing a coatable core for a modified release drug formulation for oral administration, the coatable core having a high drug load of at least 70 wt % based on the total weight of the coatable core, the method comprising:

granulating a composition comprising a drug and at least one binder to form granules;

blending the granules with a pharmacologically acceptable disintegrant and optionally one or more additional pharmacologically acceptable excipients to form a compression blend, wherein the disintegrant is present in an amount from about 0.5 wt % to about 5 wt %, based on the total weight of the coatable core; and compressing the compression blend using an external lubrication compression method to form the coatable core.

The method of the present invention advantageously produces coatable cores having a low friability, high hardness, rapid disintegration time and fast drug release, which could not have been expected or predicted from the art.

DETAILED DESCRIPTION OF THE INVENTION

Figure 1:
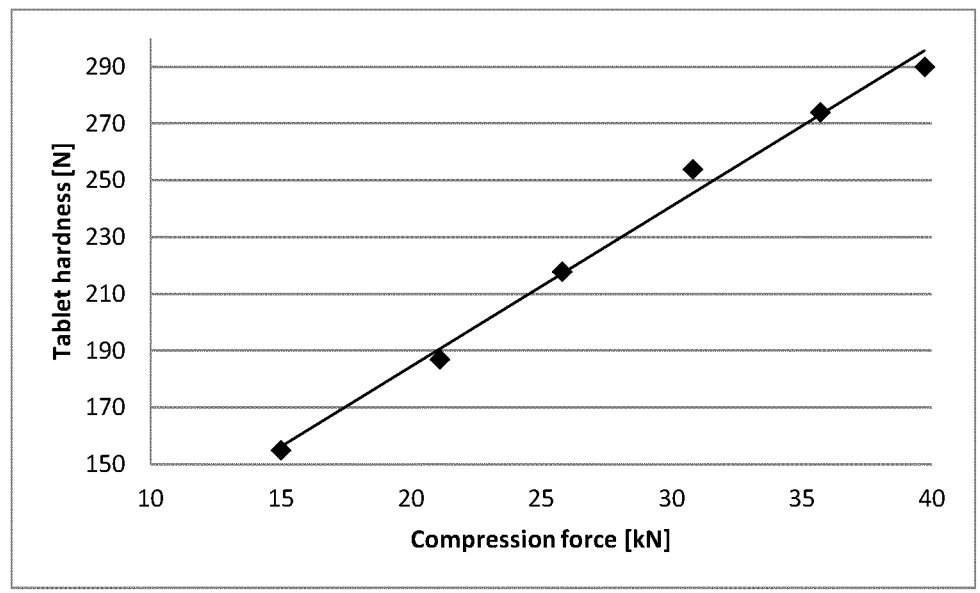
FIG. 1 shows a graph depicting the correlation between compression force and tablet hardness for 1600 mg 5-ASA tablet cores produced using external lubrication according to Examples 2A-2G.

The granules can be formed using a wet granulation or a dry granulation process. In embodiments where the granules are formed using a wet granulation process, the composition comprising the drug and a least one binder further comprises a granulation liquid.

The granulation liquid may include, but is not limited to water, an organic solvent, a hydro-alcoholic mixture (e.g. a water/ethanol mixture or a water/isopropanol mixture), or a hydro-organic (e.g. a water/acetone mixture). Suitable organic solvents include but are not limited to ethanol, isopropyl alcohol, acetone, dichloromethane, and combinations thereof. Preferably, the granulation liquid is water.

The binder can be added as a solution with the granulation liquid or can be part of the powder bed which is then granulated with the granulation liquid.

The binder can be any suitable binder known by the skilled person, for example a sugar or a polymer. Preferred synthetic polymer binders include, but are not limited to hydroxypropyl cellulose, hydroxypropyl methylcellulose (HPMC or hypromellose, e.g. Pharmacoat® 603), microcrystalline cellulose (e.g. Avicel® pH 102), methylcellulose, ethylcellulose, polyvinylpyrolidone (PVP), sodium carboxymethyl cellulose, polyvinyl alcohol (PVA), polyethylene glycol 4000 (PEG 4000), and polyethylene glycol 6000 (PEG 6000). Preferred natural polymer binders include, but are not limited to starch, modified starch, pre-gelatinised starch, acacia gum, guar gum, tragacanth gum, xantham gum, gelatine, sucrose solution and maltodextrin solution. The binder is preferably present in an amount of about 3 wt % or less, preferably about 2 wt % or less, more preferably about 1 wt % or less, and most preferably about 0.5 wt % or less, based on the total weight of the coatable core.

Granulation can be carried out using any suitable mixer or granulator known in the art. For example, wet granulation can be carried out using heavy duty mixing equipment such as a kneader or a high shear mixer granulator. Examples of suitable machines include a Hobart mixer, a Sigma type kneader, a V-blender with intensifier bars, a Lödige mixer chopper, a Diosna high shear mixer and a GEA high shear mixer. Granulation can also be carried out using a fluid bed drier (e.g. a Diosna fluid bed drier or a GEA fluid bed drier). It is preferred that granulation is carried out using a high shear mixer granulator. Granulation is typically carried out for a length of time sufficient to produce granules of the required bulk density and with acceptable low levels of residual solvents.

In embodiments where the granules are formed using a wet granulation process, the wet granules are dried prior to blending. Preferably, the wet granules are dried such that the dry granules have a moisture content (loss on drying) in the range of from less than about 0.6%, more preferably less than about 0.4%, more preferably less than about 0.3%, and most preferably less than about 0.2%. Loss on drying (LOD) is determined according to the European Pharmacopoeia (Ph. Eur. 2.2.32). Preferably, the granules are sieved before and/or after drying to break up any large lumps or agglomerates.

The granules are blended with a pharmacologically acceptable disintegrant and optionally one or more additional pharmacologically acceptable excipients to form a compression blend. Preferably, the excipients are pre-blended before blending with the granules. Optional pharmacologically acceptable excipients include, but are not limited to a filler or diluent material, e.g. lactose or cellulose material such as microcrystalline cellulose (e.g. Vivapur® 102), and a flow regulator, e.g. colloidal silicon dioxide (e.g. Aerosil® 200).

The disintegrant is present in an amount from about 0.5 wt % to about 5 wt %, based on the total weight of the coatable core. Preferably, the disintegrant is present in in an amount of about 0.5 wt % to about 3 wt %, based on the total weight of the coatable core. The disintegrant can be any suitable disintegrant known by the skilled person, e.g. croscarmellose sodium (e.g. Ac-Di-Sol®, Nymcel® ZSX, Primellose®, Solutab® and Vivasol®), crosslinked polyvinylpyrolidone (e.g. Kollidon® and Polyplasdone™), crosslinked alginic acid (e.g. Alginic acid NF and Satialgine®), calcium silicate, and sodium starch glycolate (e.g. Explotab® and Vivastar® P). A particularly preferred disintegrant is sodium starch glycolate.

The compression blend is compressed using an external lubrication compression process. External lubrication is when a lubricant is applied to the tableting machine (e.g. a tablet press). The lubricant can be applied to the dies and/or the punches of the tableting machine. Typically, the lubricant is sprayed onto the dies and/or punches in a dry state using an external lubrication system such as a Matsui Exlub system or a Pharma Spray system by Pharma Technology. The exact operating parameters are dependent upon the system used. Preferably, the lubricant is sprayed onto the dies and/or punches of the tableting machine at a dosing rate of from about 300 to about 500 g/h, more preferably from 350 to about 450 g/h, with an atomisation air pressure of from about 30 kPa to 50 kPa, and a pressure of dust extraction of from about 250 to about 500 Pa. This system allows consistent amounts of lubricant to be applied to the tablets throughout a batch, and from one batch of tablets to another. Excess lubricant is eliminated using a vacuum system.

The compression blend itself may optionally comprise one or more pharmacologically acceptable lubricants, i.e. an internal lubricant. The internal lubricant is preferably present in the compression blend in an amount of about 0.5 wt % or less, preferably about 0.25 wt % or less, more preferably about 0.1 wt % or less, and most preferably about 0.05 wt % or less, based on the total weight of the coatable core.

The external or internal lubricant can be any suitable lubricant known by the skilled person. Preferred lubricants include by are not limited to magnesium stearate, calcium stearate, stearic acid, hydrogenated vegetable oil (e.g. Sterotex®, Lubritab® and Cutina®), mineral oil, polyethylene glycol 4000-6000, sodium lauryl sulfate (SLS), glyceryl palmitostearate (e.g. Precirol®), glyceryl behenate (Compitrol® 888), sodium benzoate or sodium stearate fumarate. A particularly preferred lubricant is magnesium stearate.

Compression of the compression blend can be carried out using any suitable tableting machine known in the art. An example of a suitable tableting machine is a rotary tablet machine (e.g. a Fette P1200 tableting machine). The exact operating parameters for the tableting machine are dependent upon the machine used.

Preferably, the compression speed during the compression step is from about 1,000 to about 60,000 tablets per hour, preferably from about 10,000 to about 50,000 per hour, more preferably from about 15,000 to about 40,000 per hour, more preferably from about 25,000 to about 35,000 tablets per house, e.g. about 30,000 tablets per hour. A compression speed greater than about 30,000 tablets per hour generally has a negative impact on the quality of the core.

The compression force depends on the compressibility of the compression blend and the desired physical properties of the tablet cores. A typical compression force for use in the method of the present invention is in the range of from about 25 to about 35 kN, e.g. about 29 kN.

It is preferred that the granules have a bulk density of at least about 450 g/l to about 750 g/l, preferably from about 540 g/l to about 700 g/l. Bulk density is measured by weighing 100 g of dried granules in a graduated cylinder and recording the volume according to the European Pharmacopoeia (Ph. Eur. 2.9.34).

It is preferred that the compression blend has a bulk density of at least about 500 g/l to about 800 g/l, preferably from about 600 g/l to about 750 g/l. Preferably, the compression blend has a moisture content (LOD) in the range of from about 0.5% to about 1.4%, more preferably from about 0.7% to about 1.0%, most preferably from about 0.7% to about 0.8%.

According to a second aspect of the present invention, there is provided a coatable core for a modified release drug formulation for oral administration, the coatable core having a high drug load of at least 70 wt %, based on the total weight of the coatable core, the core comprising:
   a drug in an amount of more than about 1200 mg;
   a pharmacologically acceptable lubricant in an amount of less than about 0.5 wt %, based on the total weight of the coatable core;
   a pharmacologically acceptable disintegrant in an amount of from about 0.5 wt % to about 5 wt %, based on the total weight of the coatable core; and
   optionally one or more additional pharmacologically acceptable excipients.

According to a third aspect of the present invention, there is provided a delayed release drug formulation for oral administration to deliver a drug to the intestine of a subject, said formulation comprising:
   a coatable core having a high drug load of at least 70 wt %, based on the total weight of the coatable core, the comprising:
      a drug in an amount of more than about 1200 mg;
      a pharmacologically acceptable lubricant in an amount of less than about 0.5 wt %, based on the total weight of the coatable core;
      a pharmacologically acceptable disintegrant in an amount of from about 0.5 wt % to about 5 wt %, based on the total weight of the coatable core; and
      optionally one or more additional pharmacologically acceptable excipients;
   a coating for the core, the coating comprising an outer layer, and optionally at least one layer between the core and the outer layer selected from the group consisting of an isolation layer and an inner layer;
   said outer layer comprising a film-forming enteric polymer having a pH threshold at about pH 5 or above, and optionally an enzymatically degradable polymer that is degraded by colonic bacterial enzymes;
   said inner layer comprising a polymeric material which is soluble in intestinal fluid or gastrointestinal fluid, said polymeric material being selected from the group consisting of a polycarboxylic acid polymer that is at least partially neutralised, and a non-ionic polymer, provided that, where said polymeric material is a non-ionic polymer, said inner layer comprises at least one additive selected from a buffer agent and a base; and
   said isolation layer comprising a non-ionic polymer which is soluble in intestinal fluid or gastrointestinal fluid.

According to a fourth aspect of the present invention, there is provided a method of producing a delayed release drug formulation for oral administration to deliver a drug to the colon according to the first aspect in which the method comprises:
   forming a core comprising a drug according to the method of the first aspect of the present invention;
   coating the core using at least one coating preparation selected from the group consisting of an isolation layer coating preparation comprising a non-ionic polymer that is soluble in intestinal fluid or gastrointestinal fluid, in a solvent system, and an inner layer coating preparation comprising a polymeric material that is soluble in intestinal fluid or gastrointestinal fluid, in a solvent system, to form an intermediate coated core; and
   coating the intermediate coated core with an outer layer coating preparation comprising a film-forming enteric polymer having a pH threshold at about pH 5 or above, and optionally an enzymatically degradable polymer that is degraded by colonic bacterial enzymes, in a solvent system, to form an outer coated core;
   wherein said polymeric material that is soluble in intestinal fluid or gastrointestinal fluid is selected from the group consisting of a polycarboxylic acid polymer that is at least partially neutralised, and a non-ionic polymer, provided that, where said polymeric material is a non-ionic polymer, said inner layer comprises at least one additive selected from a buffer agent and a base.

The core may be coated directly using either said isolation layer coating preparation or said inner layer coating preparation, to form said intermediate coated core. Alternatively, the core may be coated directly using said isolation layer coating preparation to form an isolation layer coated core which is then coated directly using said inner layer coating preparation to form said intermediate coated core.

In the alternate embodiments having both an isolation layer and an inner layer where the third polymeric material of the inner layer is a non-ionic polymer, different non-ionic polymers may be used. However, it may be preferred that the same non-ionic polymer is used for the third polymeric material as the non-ionic polymer of the isolation layer in these embodiments.

The solvent system of the inner coating preparation is preferably aqueous.

In embodiments where the outer layer coating preparation comprises both a film-forming enteric polymer and an enzymatically degradable polymer, the outer layer coating preparation is preferably formed by combining said enzymatically degradable polymer in an aqueous medium (or solvent) with said film-forming enteric polymer in an organic medium (or solvent).

The organic medium may be selected from the group consisting of $C_1$ to $C_4$ alcohols; methyl glycol; butyl glycol; acetone; methyl glycol acetate; and mixtures thereof. However, the organic medium preferably comprises ethanol. In preferred embodiments, the organic medium is 85 to 98% ethanol, e.g. about 96% ethanol.

The organic medium may contain from about 2% to about 10%, e.g. about 6%, polymer solids.

The aqueous medium may be selected from the group consisting of water; $C_1$ to $C_6$ alcohol; and mixtures thereof. However, the aqueous medium is preferably a mixture of water and a $C_1$ to $C_6$ alcohol, preferably butan-1-ol. The ratio of water to alcohol in such mixtures is at least 5:1, preferably about 11:1.

Release from formulations according to the present invention is typically delayed until at least the distal ileum and, preferably, the colon. Release from certain formulations may also be sustained. However, in preferred formulations, release is pulsatile.

The time between initial exposure to conditions suitable for drug release and the start of drug release is known as the "lag time". The lag time depends on a number of factors including coating thickness and composition and may vary from one patient to the next. Formulations according to the present invention usually display a lag time in colonic conditions of at least 10 minutes. In most embodiments, the lag time is from about 10 minutes to about 8 hours. In certain cases, complete release of the drug may be achieved in no more than 5 hours, e.g. no more than 4 hours, after exposure to these conditions.

A formulation is usually defined as gastric resistant if there is less than 10 wt % drug release in acidic media after 2 hours. Formulations according to the present invention typically display far less than 10 wt % drug release in acidic media and may be considered to be gastric resistant. The formulations usually display less than 1 wt % drug release in acidic media and, typically, display substantially no drug release in acidic media. When starch is combined with an acrylate film-forming material to form the outer layer of the coating for the core, typically less than 5% drug release occurs over 5 hours in conditions simulating the stomach and small intestine.

Coatable Core

The coatable core ("core") is a solid body formed by compression on which a coating can be applied. In preferred embodiments, the coatable core is a tablet.

The core may be uncoated or, the core may be pre-coated with an isolation layer and/or an inner layer onto which the outer layer coating is directly applied. The isolation layer and the inner layer are discussed in more detail below.

The core comprises at least one drug. The core according to embodiments of the present invention is designed to be used in formulations to administer a wide range of drugs. The core typically comprises a single drug as the sole therapeutically active component. However, more than one drug may be administered in a single coatable core.

Suitable drugs include those drugs which are known for intestinal administration using known delayed release oral formulations. The present invention may be used to administer drugs having a local or a systemic effect.

The identity of the drug(s) in the core obviously depends on the condition to be treated. In this connection, the present invention has particular application in the treatment of IBD (including Crohn's disease and ulcerative colitis); IBS; constipation; diarrhoea; infection; and carcinoma, particularly colon or colorectal cancer.

The present invention has particular application in the intestinal administration of a drug comprising at least one acidic group such as a carboxylic acid group. Such drugs may be acidic drugs or zwitterionic drugs. An example of such a drug is 5-aminosalicylic acid ("5-ASA" or mesalazine).

For the treatment or prevention of IBD, the core may comprise at least one drug selected from the group consisting of anti-inflammatory agents (e.g. 5-ASA); steroids (e.g. prednisolone; budesonide or fluticasone); immunosuppressants (e.g. azathioprine; cyclosporin; and methotrexate); and antibiotics; and biological agents including peptides, proteins and antibody fragments. Suitable examples of biological agents include alkaline phosphatase and anti-TNF antibodies such as infliximab, adalimumab, certulizumab pegol, golimumab and ustekinumab.

For the treatment or prevention of cancer, the core may comprise at least one antineoplastic agent. Suitable antineoplastic agents include fluorouracil; methotrexate; dactinomycin; bleomycin; etoposide; taxol; vincristine; doxorubicin; cisplatin; daunorubicin; VP-16; raltitrexed; oxaliplatin; and pharmacologically acceptable derivatives and salts thereof. For the prevention of colon cancer or colorectal cancer, primarily in patients suffering from colitis, the formulation may comprise anti-inflammatory agents, 5-ASA, sulindac, celecoxib and/or eflornithine (DFMO).

For the treatment or prevention of IBS, constipation, diarrhoea or infection, the core may comprise at least one active agent suitable for the treatment or prevention of these conditions.

Pharmacologically acceptable derivatives and/or salts of the drugs may also be used in the coatable core. An example of a suitable salt of prednisolone is methyl prednisolone sodium succinate. A further example is fluticasone propionate.

The present invention has particular application in either the treatment of IBD (particularly, ulcerative colitis) or the prevention of colon cancer or colorectal cancer (primarily in colitis patients), both using 5-ASA. It also has application as a portal of entry of drugs into the systemic circulation via the colon. This is particularly advantageous for peptide and protein drugs which are unstable in the upper gastrointestinal tract. The present invention may also be utilised for the purpose of chronotherapy.

The core has a high drug load of at least about 70 wt %, based on the total weight of the coatable core. Preferably the core has a drug load of from about 75 wt % to about 95 wt %, or from about 80 wt % to about 95 wt %, e.g. from about 85 wt % to about 90 wt %.

The method according to the first aspect of the present invention can be used to produce any size core for, example the drug can be present in the core in an amount of from about 350 mg to about 1650 mg, or from about 450 mg to about 1650 mg, or from about 750 mg to about 1650 mg, or from about 1150 mg to about 1650 mg, or from about 1450 mg to about 1650 mg, or from about 1550 mg to about 1650 mg. Preferably, the drug is present in the core amount selected from about 400 mg, about 800 mg, about 1200 mg, about 1500 mg, or about 1600 mg. There is a particular advantage when the method of the first aspect of the present invention used to produce cores comprising more than about 1200 mg of a drug.

In embodiments relating to the second and third aspects of the present invention, the drug is present in the core in an amount of more than about 1200 mg. It is preferred that the drug is present in the core in an amount of from about 1250 mg to about 1650 mg, or from about 1450 mg to about 1650 mg, or from about 1550 mg to about 1650 mg, or about 1600 mg.

The core further comprises a disintegrant in an amount of from about 0.5 wt % to about 5 wt %, based on the total weight of the coatable core. Preferably, the disintegrant is present in an amount of about 0.5 wt % to about 3 wt %, based on the total weight of the coatable core. The disintegrant can be any suitable disintegrant known by the skilled person, e.g. croscarmellose sodium (e.g. Ac-Di-Sol®) and sodium starch glycolate (e.g. Explotab® and Vivastar® P). A particularly preferred disintegrant is sodium starch glycolate.

In embodiments relating to the second and third aspects of the present invention, the core further comprises a pharmaceutically acceptable lubricant in an amount of less than about 0.5 wt %, based on the total weight of the coatable core. Preferably, the lubricant is present in an amount of about 0.25 wt % or less, more preferably about 0.1 wt % or less, most preferably about 0.05 wt % or less, based on the total weight of the coatable core. Preferred lubricants are as detailed above.

The core may further comprise one or more additional pharmacologically acceptable excipients as detailed above. In this connection, the core typically consists of a mixture of the drug(s) with a filler or diluent material, e.g. lactose or cellulose material such as microcrystalline cellulose; a binder, e.g. hydroxypropyl methylcellulose (HPMC) or microcrystalline cellulose; a disintegrant, e.g. croscarmellose sodium or sodium starch glycolate, a flow regulator, e.g. colloidal silicon dioxide, and/or a lubricant, e.g. magnesium stearate.

It is preferred that the core has a friability of 0% to less than about 0.5%, preferably from 0% to less than about 0.25%, more preferably from about 0% to less than about 0.2%, most preferably from 0% to less than about 0.1%. Friability is defined as the tendency for a tablet or tablet core to chip, crumble or break following compression. Friability is measured using a friability tester according to the European Pharmacopoeia (Ph. Eur. 2.9.7).

It is preferred that the core has a disintegration time in water of less than about 10 minutes, preferably less than about 5 minutes as measured according to the European Pharmacopoeia (Ph. Eur. 2.9.1).

Preferably, the core has a hardness in the range of from about 200 N to about 330 N, more preferably from about 230 N to about 300 N, most preferably from about 250 N to about 280 N. Tablet core hardness is measured using a tablet hardness tester according to the European Pharmacopoeia (Ph. Eur. 2.9.8).

The core preferably has a height (thickness) between about 8.5 and about 9.2 mm. Core (tablet) thickness is typically measured using an electric calliper.

Enzymatically Degradable Polymer (First Polymeric Material)

The enzymatically degradable polymer is degraded by one or more bacterial enzymes found in the colon of a subject (colonic bacterial enzymes). Such enzymes are produced by colonic bacteria and include amylases such as alpha-amylases, beta-amylases and iso-amylases; amylopullunase, glucoamylase, alpha-glucosidase, maltogenic-amylase, glycosyltransferases and amylomaltase.

The person skilled in the art is capable of determining whether a material is susceptible to attack by colonic bacteria using techniques comprising part of the common general knowledge. For example, a pre-determined amount of a given material could be exposed to an assay containing an enzyme from a bacterium found in the colon and the change in weight of the material over time may be measured.

The enzymatically degradable polymer is preferably a polysaccharide. Suitable polysaccharides include but are not limited to starch; amylose; amylopectin; chitosan; chondroitin sulfate; cyclodextrin; dextran; pullulan; carrageenan; sclerglucan; chitin; curdulan, levan and hemicelluloses such as xylan, glucuronoxylan, arabinoxylan, glucomannam, xyloglucan. The polysaccharide is preferably starch. Starches are usually extracted from natural sources such as cereals; pulses; and tubers. Suitable starches for use in the present invention are typically food grade starches and include rice starch; wheat starch; corn (or maize) starch; pea starch; potato starch; sweet potato starch; tapioca starch; sorghum starch; sago starch; and arrow root starch. The use of maize starch is exemplified below.

Starch is typically a mixture of two different polysaccharides, namely amylose and amylopectin. Different starches may have different proportions of these two polysaccharides. Most natural (unmodified) maize starches have from about 20 wt % to about 30 wt % amylose with the remainder being at least substantially made up of amylopectin.

Suitable starches include "high amylose" and "low amylose" starches. High amylose starches are particularly preferred.

"High amylose" starches, are starches having at least 50 wt % amylose. Particularly suitable starches have from about 50 wt % to about 75 wt % amylose, preferably from about 50 wt % to about 70 wt %, more preferably from about 50 wt % to about 65 wt %, most preferably from about 50 wt % to about 60 wt %, e.g. about 55 wt %.

"Low amylose" starches are starches having less than 50 wt % amylose and at least 50 wt % amylopectin, e.g. up to 75 wt % amylopectin and even as much as up to 99 wt % amylopectin.

Starches suitable for use in the present invention typically have at least 0.1 wt %, e.g. at least 10 wt % or 15 wt %, preferably at least 35 wt %, amylose. Such starches have no more than 99.9 wt %, e.g. no more than 90 wt % or 85 wt %, preferably no more than 65 wt %, amylopectin. Such starches may have up to about 99 wt % amylose and no less than 1 wt % amylopectin Starches suitable for use in the present invention may have up to 100% amylopectin, more typically from about 0.1 wt % to about 99.9 wt % amylopectin. The starch may be, for instance, unmodified waxy corn starch. This typically comprises about 100% amylopectin.

Preferred starches have no more than 50 wt % amylopectin. Particularly suitable starches have from about 25 wt % to about 35 wt % amylopectin, e.g. about 30 wt % amylopectin.

The person skilled in the art is capable of determining the relative proportions of amylose and amylopectin in any given starch. For example, near-infrared (NIR) spectroscopy could be used to determine the amylose and amylopectin content of a starch using calibration curves obtained by NIR using laboratory-produced mixtures of known amounts of these two components. Further, starch could be hydrolysed to glucose using amyloglucosidase. A series of phosphorylation and oxidation reactions catalysed by enzymes result in the formation of reduced nicotinamide adenine dinucleotide phosphate (NADPH). The quantity of NADPH formed is stoichiometric with the original glucose content. Suitable test kits for this procedure are available (e.g. R-Biopharm GmbH, Germany). Another method that could be used involves subjecting the coating to digestion by bacterial enzymes, e.g. α-amylase, to produce short chain fatty acids (SOFA) which can be quantified by gas-liquid chromatography using a capillary column.

Preferred starches are "off-the-shelf" starches, i.e. starches which require no processing prior to use in the context of the present invention. Examples of particularly suitable "high amylose" starches include Eurylon® 6 and Amylo N-400 (Roquette, Lestrem, France) or Amylogel 03003 (Cargill, Minneapolis, USA) all of which are examples of a maize starch having about 50-70 wt % amylose.

In a preferred embodiment, it has been found that a mixture of two suitable polymers at an appropriate ratio, applied as a film coating on to a core, at least minimises, and can substantially eliminate, drug release in the stomach and small intestine. Subsequent drug release in the colon is believed to occur by the combined active physiological triggers: i.e. by dissolution of the second material, particularly Eudragit® S, and digestion of the first material, e.g. starch or amylose.

Film-Forming Enteric Polymer (Second Polymeric Material)

The film-forming enteric polymer is pH sensitive and has a pH threshold at about pH 5 or above. The "pH threshold" is the pH below which it is insoluble and at or above which it is soluble. The pH of the surrounding medium therefore triggers dissolution of the polymeric material. Thus, none (or essentially none) of the enteric polymer dissolves below the pH threshold. Once the pH of the surrounding medium reaches (or exceeds) the pH threshold, the second material becomes soluble.

By "insoluble" we mean that 1 g of the second material requires more than 10,000 ml of solvent (surrounding medium) to dissolve at a given pH.

By "soluble", we mean that 1 g of the second material requires less than 10,000 ml, preferably less than 5,000 ml, more preferably less than 1000 ml, even more preferably less than 100 ml or 10 ml of solvent to dissolve at a given pH.

"Surrounding medium" preferably means the medium in the gastro intestinal tract, such as the gastric juice or intestinal juice. Alternatively, the surrounding medium may be the in vitro equivalent of the medium in the gastrointestinal tract.

The normal pH of gastric juice is usually in the range of 1 to 3. The enteric polymer is insoluble below pH 5 and soluble at about pH 5 or above and, thus, is usually insoluble in gastric juice. Such a material may be referred to as a gastro-resistant material.

The enteric polymer has a pH threshold of pH 5 or above, e.g. about pH 5.5 or above, preferably about pH 6 or above, and more preferably about pH 6 or above. The enteric polymer typically has a pH threshold of no more than about pH 8, e.g. no more than about pH 7.5 and preferably no more than about pH 7.2. Preferably, the second polymeric material has a pH threshold within the range of pH found in intestinal fluid.

The pH of intestinal fluid may vary from one person to the next, but in healthy humans is generally from about pH 5 to 6 in the duodenum, from about 6 to 8 in the jejunum, from about 7 to 8 in the ileum, and from about 6 to 8 in the colon. The second polymeric material preferably has a pH threshold of about 6.5, i.e. is insoluble below pH 6.5 and soluble at about pH 6.5 or above, and more preferably has a pH threshold of about 7, i.e. is insoluble below pH 7 and soluble at about pH 7 or above.

The pH threshold at which a material becomes soluble may be determined by a simple titration technique which would be part of the common general knowledge to the person skilled in the art.

Examples of suitable film-forming enteric polymers include an acrylate polymer, a cellulose polymer or a polyvinyl-based polymer. Examples of suitable cellulose polymers include cellulose acetate phthalate (CAP); cellulose acetate trimellitate (CAT); hydroxypropyl methylcellulose phthalate (HPMCP) and hydropropylmethylcellulose acetate succinate. Examples of suitable polyvinyl-based polymers include polyvinyl acetate phthalate (PVAP).

The film-forming enteric polymer is preferably a co-polymer of a (meth)acrylic acid and a (meth)acrylic acid $C_{1-4}$ alkyl ester, for instance, a copolymer of methacrylic acid and methacrylic acid methyl ester. Such a polymer is known as a poly(methacrylic acid/methyl methacrylate) co-polymer. Suitable examples of such co-polymers are usually anionic and not sustained release polymethacrylates. The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight (MW) of preferred anionic co-polymers is usually from about 120,000 to 150,000, preferably about 135,000.

Preferred anionic poly(methacrylic acid/methyl methacrylate) co-polymers include Eudragit® L (acid:ester ratio about 1:1; MW about 135,000; pH threshold of about 6); Eudragit® S (acid:ester ratio about 1:2; MW about 135,000; pH threshold of about 7); and Eudragit® FS (a poly(methyl acrylate/methyl methacrylate/methacrylic acid); acid:ester ratio of about 1:10; MW about 220,000; pH threshold of about 7).

The film-forming enteric polymer may be a copolymer of methacrylic acid and ethyl acrylate. Eudragit® L100-55 poly(methacrylic acid/ethyl acrylate); acid:ester ratio of about 1:1; MW about 250,000; pH threshold of about 6. The Eudragit® co-polymers are manufactured and/or distributed by Evonik, Darmstadt, Germany.

Mixtures of film-forming enteric polymers may be used as appropriate. An example of a suitable mixture would include a mixture, e.g. a 1:1 mixture, of Eudragit® L and Eudragit® S. However, the use of a particular film-forming polymer material, e.g. a poly(methacrylic acid/methyl methacrylate) co-polymer, alone is preferred.

The use of Eudragit® S alone as the film-forming enteric polymer is particularly preferred.

Outer Layer

The proportion of the enzymatically degradable polymer to the film-forming enteric polymer is typically at least 1:99, e.g. at least 10:90 and preferably at least 25:75. The proportion is typically no more than 99:1, e.g. no more than 75:25 and preferably no more than 60:40. In some embodiments, the proportion may be no more than 35:65. In some preferred embodiments, the proportion is from 10:90 to 75:25, e.g. from 10:90 to 60:40 and preferably from 25:75 to 60:40. In some particularly preferred embodiments, the proportion is from 15:85 to 35:65, e.g. from 25:75 to 35:65 and preferably about 30:70. In other particularly preferred embodiments, the proportion is from 40:60 to about 60:40, e.g. about 50:50.

Optionally, conventional excipients such as those excipients selected from plasticisers for film formation (for example, triethyl citrate), anti-tack agents (such as glyceryl monostearate or GMS) and surfactants (such as polysorbate 80), may be included in amounts up to 30 wt % of the final composition of the outer coating preparation.

The thickness of the outer layer coating of the core is typically from about 10 μm to about 150 μm. The thickness of a specific coating will, however, depend on the composition of the coating and the size of the core. For example, coating thickness is directly proportional to the amount of polysaccharide in the coating. Thus, in embodiments where the coating comprises high amylose starch and Eudragit® S at a ratio of between about 30:70 and 60:40, the coating thickness may be from about 70 μm to about 130 μm, and preferably from about 90 μm to about 110 μm.

The amount of enteric polymer in the outer coating is not related to the size of the core. The outer layer typically has a coating amount of enteric polymer of about 2 mg/cm$^2$ to about 10 mg/cm$^2$, e.g. from about 2 mg/cm$^2$ to about 8 mg/cm$^2$, or from about 3 mg/cm$^2$ to about 8 mg/cm$^2$, or from about 4 mg/cm$^2$ to about 8 mg/cm$^2$, or from about 6 mg/cm$^2$ to about 8 mg/cm$^2$, or from about 7 mg/cm$^2$ to about 8 mg/cm$^2$, e.g. about 7.5 mg/cm$^2$, based on the dry weight of the enteric polymer. A typical core has a diameter of from about $5 \times 10^{-4}$ m to about 25 mm.

Inner Layer

The formulation according to the present invention optionally comprises an inner layer between the core and the outer layer. The inner layer comprises a third polymeric material which is soluble in intestinal fluid or gastrointestinal fluid (both gastric and intestinal fluid).

By "gastric fluid", the inventors mean the aqueous fluid in the stomach of a mammal, particularly a human. The fluid contains up to about 0.1 N hydrochloric acid and substantial quantities of potassium chloride and sodium chloride, and plays a key role in digestion by activating digestive enzymes and denaturing ingested protein. Gastric acid is produced by cells lining the stomach and other cells produce bicarbonate which acts as a buffer to prevent the gastric fluid from becoming too acidic.

By "intestinal fluid", the Inventors mean the fluid in the lumen of the intestine of a mammal, particularly a human. Intestinal fluid is a pale yellow aqueous fluid secreted from glands lining the walls of the intestine. Intestinal fluid includes fluid found in the small intestine, i.e. fluid found in the duodenum (or "duodenal fluid"), fluid found in the jejunum (or "jejunal fluid") and fluid found in the ileum (or "ileal fluid"), and fluid found in the large intestine, e.g. "colonic fluid".

The skilled person can readily determine whether a polymer is soluble in gastric fluid and/or intestinal fluid. If a polymer is soluble in water (or aqueous solution, e.g. a buffer solution) at a pH from 1 to 3, then that polymer would typically be soluble in gastric fluid. Similarly if a polymer is soluble in water (or aqueous solution, e.g. a buffer solution) at a pH from 5 to 8, then that polymer would typically be soluble in intestinal fluid. Alternatively, the compositions of gastric fluid and intestinal fluid are known and may be replicated in vitro. If a polymer is soluble in artificial gastric fluid or intestinal fluid in vitro, then it would typically be soluble in gastric fluid or intestinal fluid respectively in vivo.

Any pharmacologically acceptable water-soluble film-forming polymers are, in principle, suitable for use as the third polymeric material. The solubility of the water-soluble polymers may be dependent on pH, i.e. the polymeric material may be a pH sensitive polymer having a pH threshold.

The polymeric material may be soluble in at least one fluid selected from gastric fluid, duodenal fluid, jejunal fluid and ileal fluid. However, in preferred embodiments, the solubility of the third polymeric material in water is not dependent on pH; at least not within the range of pH found in the intestine. In preferred embodiments, the third polymeric material is soluble in fluid at any point in the stomach and intestine, i.e. in gastrointestinal fluid.

Suitable polymers for use as the third polymeric material preferably contain groups that are ionisable in aqueous media to form anions. Such polymers are known in the art as "anionic" polymers. Suitable anionic polymers include polycarboxylic acid polymers, i.e. polymers or co-polymers that contain a plurality of carboxylic acid functional groups that are ionisable in aqueous media such as intestinal fluid, to form carboxylate anions.

In embodiments in which the third polymeric material is a polycarboxylic acid polymer, it is preferred that the third polymeric material is at least partially neutralised, i.e. that at least a portion, e.g. at least 10%, preferably at least 25%, more preferably at least 50%, and most preferably at least 90%, of the carboxylic acid groups are in the form of carboxylate anions. In particularly preferred embodiments, all of the carboxylic acid groups in the third polymeric material are in the form of carboxylate anions. Such polymers are referred to herein as "fully neutralised".

In preferred embodiments, the second and third polymeric materials are based on the same polycarboxylic acid polymer with the third polymeric material having a higher degree of neutralisation than the second polymeric material. For example, for a particular polycarboxylic acid polymer, the second polymeric material may be in non-neutralised form with the third polymeric material in partially or fully neutralised form. Alternatively, the second polymeric material may be in partially neutralised form, with the third polymeric material also in partially neutralised form (although partially neutralised to a greater extent), or in fully neutralised form.

Examples of suitable polycarboxylic acid polymers include cellulose acetate phthalate (CAP), polyvinyl acetate phthalate (PVAP), hydroxypropyl methylcellulose phthalate (HPMCP), hydroxypropyl methylcellulose acetate succinate (HPMC-AS), cellulose acetate trimellitate (CAT), xanthan gum, alginates and shellac. However, the polycarboxylic acid polymer is preferably selected from co-polymers of a (meth)acrylic acid and a (meth)acrylic acid alkyl, e.g. $C_{1-4}$ alkyl, ester and a copolymer of methacrylic acid and methacrylic acid methyl ester is particularly suitable. Such a polymer is known as a poly(methacrylic acid/methyl methacrylate) co-polymer or a "polymethacrylate". The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight ("MW") of preferred anionic co-polymers is usually from about 120,000 to 150,000, preferably about 125,000 or about 135,000.

Preferred co-polymers for the third polymeric material are discussed in detail in the section above relating to the second polymeric material, and include Eudragit® L; Eudragit® S; Eudragit® FS 30 D; Eudragit® L30D-55; and Eudragit® L100-55.

Preferably, the exemplary polymers are used as the third polymeric material is in at least partially, more preferably fully, neutralised form.

Partially neutralised polymers suitable for use as the third polymeric material, and their methods of production, are known in the art, for example from US2008/0200482A and WO2008/135090A. These polymers may be fully neutralised by the addition of further base to the coating solutions.

In preferred embodiments, the third polymeric material is an at least partially, preferably fully, neutralised co-polymer of (meth)acrylic acid and a (meth)acrylic acid $C_{1-4}$ alkyl ester. In particularly preferred embodiments, the third polymeric material is a fully neutralised co-polymer of (meth)acrylic acid and (meth)acrylic acid methyl ester, particularly Eudragit® S. The Inventors have observed that fully neutralised Eudragit® S is capable of forming a film and is readily and completely soluble in water independently of at least the range of pH found in the intestine, e.g. about pH 5 to about pH 8. Fully neutralised Eudragit® S is particularly preferred for use as the third polymeric material in the present invention.

Other polymers suitable for use as the third polymeric material include pharmacologically acceptable non-ionic polymers, i.e. pharmacologically acceptable polymers which do not ionise in aqueous media. In these embodiments, the inner layer additionally comprises at least one additive selected from a buffer agent and a base. In particular, the inner layer of these embodiments preferably comprises a base and, optionally, a buffer agent. In preferred embodiments, the inner layer comprises both a buffer agent and a base. Suitable examples of buffer agents and bases are discussed below.

Examples of suitable non-ionic polymers include methylcellulose (MC), hydroxypropyl cellulose (HPC), hydroxypropyl methylcellulose (HPMC), poly(ethyleneoxide)-graft-polyvinylalcohol, polyvinylpyrrolidinone (PVP), polyethylene glycol (PEG) and polyvinylalcohol (PVA). Mixtures of non-ionic polymers can be used.

Mixtures of film-forming polymer materials may be used as appropriate. The polymer components in such mixtures may be anionic polymers, non-ionic polymers, or a mixture of anionic and non-ionic polymers. An example of a suitable mixture would include a mixture, e.g. a 1:1 mixture, of Eudragit® L and Eudragit® S, and a mixture, e.g. a 1:1 mixture, of Eudragit® S and HPMC. However, the use of a particular film-forming polymeric material alone, e.g. a poly(methacrylic acid/methyl methacrylate) co-polymer and Eudragit® S in particular, is preferred.

In preferred embodiments, the inner layer comprises at least one base. The purpose of the base is to provide an alkaline environment on the underside of the outer layer once intestinal fluid begins to penetrate the outer layer. Without being bound by any particular theory, the Inventors believe that the alkaline environment facilitates dissolution and thereby also disintegration of the outer layer since the pH of the alkaline environment is above the pH threshold of the second polymeric material, thereby accelerating release of the drug from the formulation once the outer coating is dissolved and/or disintegrates.

In principle, any pharmacologically acceptable base may be used. The base is typically a non-polymeric compound. Suitable bases include inorganic bases such as sodium hydroxide, potassium hydroxide and ammonium hydroxide, and organic bases such as triethanolamine, sodium bicarbonate, potassium carbonate, trisodium phosphate, trisodium citrate or physiologically tolerated amines such as triethylamine.

The base is preferably selected from the group consisting of hydroxide bases, alkali metal bicarbonates, alkali metal carbonates, alkali metal phosphates, alkali metal citrates, or physiologically tolerated amines. More preferably, the base is a hydroxide base, and particularly preferred is sodium hydroxide.

In embodiments in which the third polymeric material is a fully neutralised polycarboxylic acid polymer, the base entrapped within the inner layer is usually the base that was used to neutralise the polymer and to adjust the pH of the inner coating preparation to a pH from about pH 7.5 to about pH 10 (see below).

In embodiments in which the third polymeric material is a non-ionic polymer, the inner layer usually comprises either a base, or more typically a combination of a base and a buffer agent.

The amount of base present in the inner layer would depend at least in part on the final pH of the inner coating preparation prior to coating a given batch of cores; the number of cores to be coated in the batch; the amount of the inner coating preparation used in the coating process of the batch.

The inner coating preferably comprises at least one buffer agent. The purpose of the buffer agent is to provide or increase buffer capacity on the underside of the outer layer once intestinal fluid begins to penetrate the outer layer. Without wishing to be bound by any particular theory, the Inventors believe that the buffer agent increases the buffer capacity in the dissolving inner layer and assists the ionisation and dissolution of the polymer in the outer layer; for a given pH, the higher the buffer capacity, the faster the rate of polymer dissolution. In embodiments where there is a base in the inner layer, the buffer agent helps maintains the alkaline environment under the outer layer once intestinal fluid penetrates the outer layer.

The buffer agent may be an organic acid such as a pharmacologically acceptable non-polymeric carboxylic acid, e.g. a carboxylic acid having from 1 to 16, preferably 1 to 3, carbon atoms. Suitable carboxylic acids are disclosed in WO2008/135090A. Citric acid is an example of such a carboxylic acid. The carboxylic acids may be used in carboxylate salt form, and mixtures of carboxylic acids, carboxylate salts or both may also be used.

The buffer agent may also be an inorganic salt such as an alkali metal salt, an alkali earth metal salt, an ammonium salt, and a soluble metal salt. As metals for the soluble metal salts, manganese, iron, copper, zinc and molybdenum can be mentioned. Further preferred, the inorganic salt is selected from chloride, fluoride, bromide, iodide, phosphate, nitrate, nitrite, sulphate and borate. Phosphates such as potassium dihydrogen phosphate are preferred over other inorganic buffer salts and organic acid buffers due to their greater buffer capacity at the pH of the coating solution, for example pH 8.

The buffer(s) is usually present in the inner layer in an amount from about 0.1 wt % to about 60 wt %, e.g. from about 0.1 wt % to about 50 wt %, preferably from about 0.1 wt % to about 40 wt %, more preferably from about 0.1 to about 20 wt %, more preferably from about 0.1 wt % to about 4 wt %, more preferably from about 0.1 wt % to about 3 wt %, and most preferably about 1 wt %, based on the dry weight of the third polymeric material.

In addition to the buffer agent and/or the base, the inner layer may comprise conventional excipients for polymer films, including those excipients selected from plasticizers (such a triethyl citrate), anti-tacking agents (such as GMS), and surfactants (such as polysorbate 80).

The thickness of the inner coating of the core is typically from about 10 μm to about 150 μm. The thickness of a specific coating will, however, depend on the composition of the coating and the size of the core.

As with the outer layer, the amount of polymer in the inner layer is not related to the size of the core. The inner layer typically has a coating about of polymer of about 2 mg/cm$^2$ to about 10 mg/cm$^2$, preferably from about 2 mg/cm$^2$ to about 8 mg/cm$^2$, and most preferably from about 3 mg/cm$^2$ to about 7 mg/cm$^2$, e.g. about 5 mg/cm$^2$, based on the dry weight of the third polymeric material.

Isolation Layer

The formulation of the present invention may have an additional (or isolation) layer either between the active core and the inner layer and/or the outer layer.

There may be formulations according to the present invention in which the composition of the core is incompatible with the delayed release coating. In such cases, it may be desirable to include an isolation layer to separate the core from the coating. For example, the present invention embraces embodiments in which the inner layer provides an alkaline environment which is thought to assist in the dissolution and degradation of the outer layer. However, if the core contains a drug having acidic groups, then the inner layer may be incompatible with the core. An example of a drug having an acidic group would be 5-ASA. In such cases, it would typically be appropriate to include an isolation layer.

Any suitable isolation layer known to the skilled person can be used. In one preferred embodiment, the isolation layer comprises a film-forming non-ionic polymer. Suitable non-ionic polymers include methylcellulose (MC); hydroxypropyl cellulose (HPC); hydroxypropyl methylcellulose (HPMC); poly(ethyleneoxide)-graft-polyvinylalcohol; polyvinylpyrollidone (PVP); polyethylene glycol (PEG); and polyvinylalcohol (PVA). Non-ionic cellulose based polymers (such as HPMC) are preferred, as is PVA. Mixtures of non-ionic polymers can also be used. A particularly preferred mixture is HPMC and PEG. The isolation layer can additionally comprise a plasticiser. Suitable plasticisers include but are not limited to polyethylene glycol, triethyl citrate, triacetin and acetyltriethyl citrate.

The formulation may also comprise an intermediate layer between the outer and inner layers, provided that the intermediate layer does not affect adversely the release characteristics of the formulation. However, the outer layer is usually provided in contact with the inner layer, that is to say the outer layer is usually applied directly on to the inner layer, i.e. there is usually no intermediate layer separating the inner and outer layers.

EXAMPLES

A number of preferred embodiments of the present invention will now be described with reference to the drawings, in which:—

Figure 2:
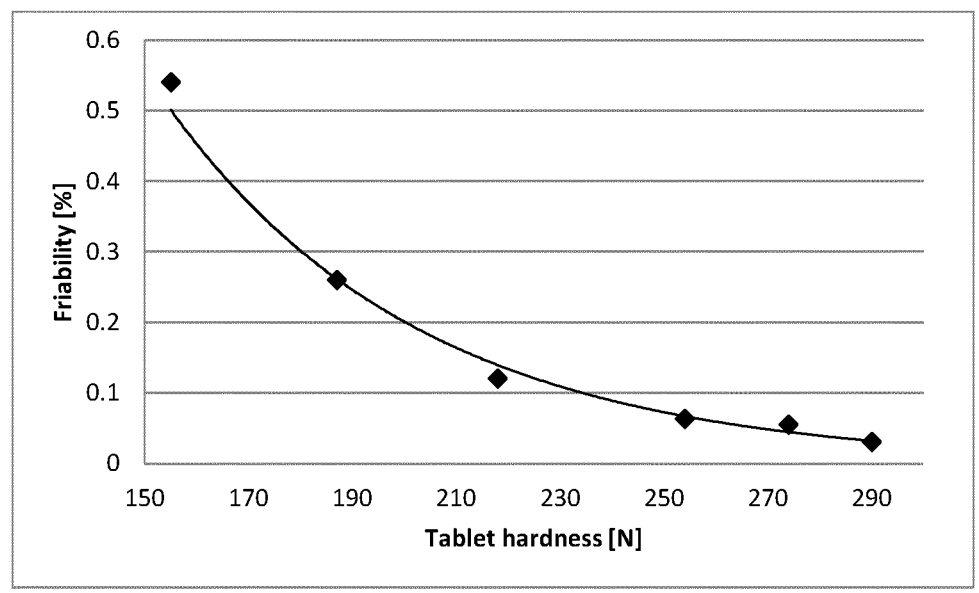
FIG. 2 shows a graph depicting the correlation between tablet hardness and friability for 1600 mg 5-ASA tablet cores produced using external lubrication according to Examples 2A-2G.
Figure 3:
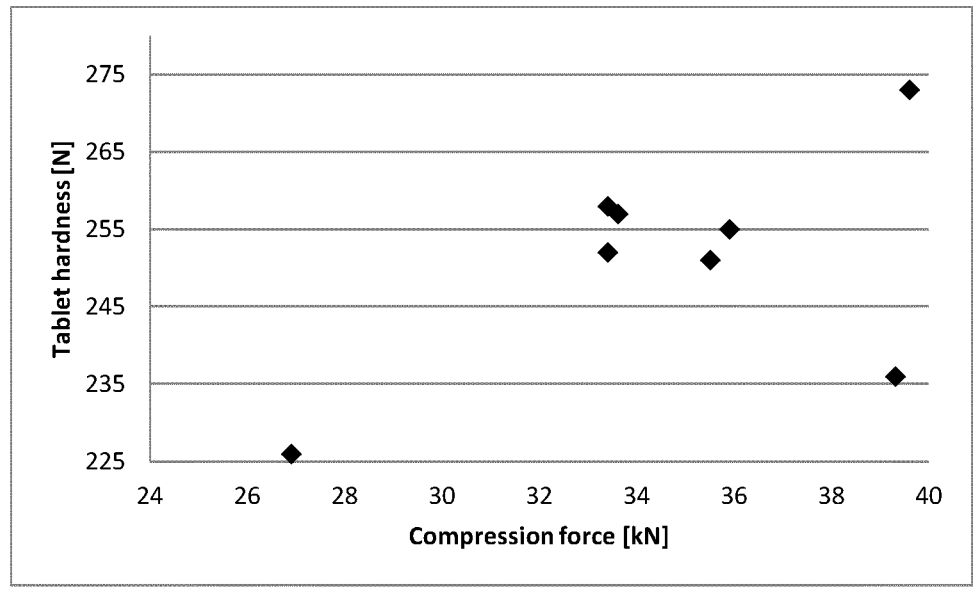
FIG. 3 shows a graph depicting the correlation between compression force and tablet hardness for 1600 mg 5-ASA tablet cores produced using internal lubrication according to Comparative Examples 3A-3H.
Figure 4:
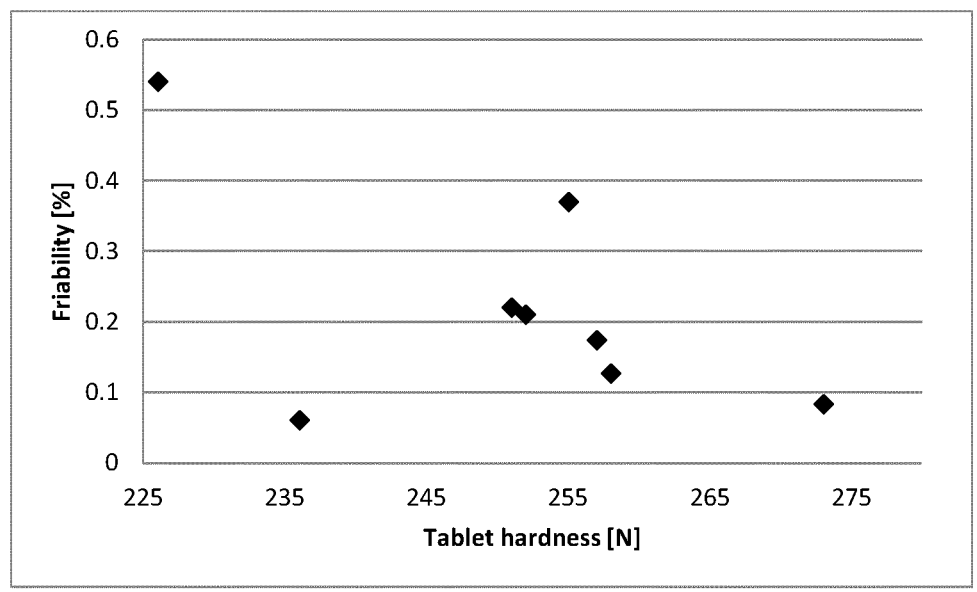
FIG. 4 shows a graph depicting the correlation between tablet hardness and friability for 1600 mg 5-ASA tablet cores produced using internal lubrication according to Comparative Examples 3A-3H.
Figure 5:
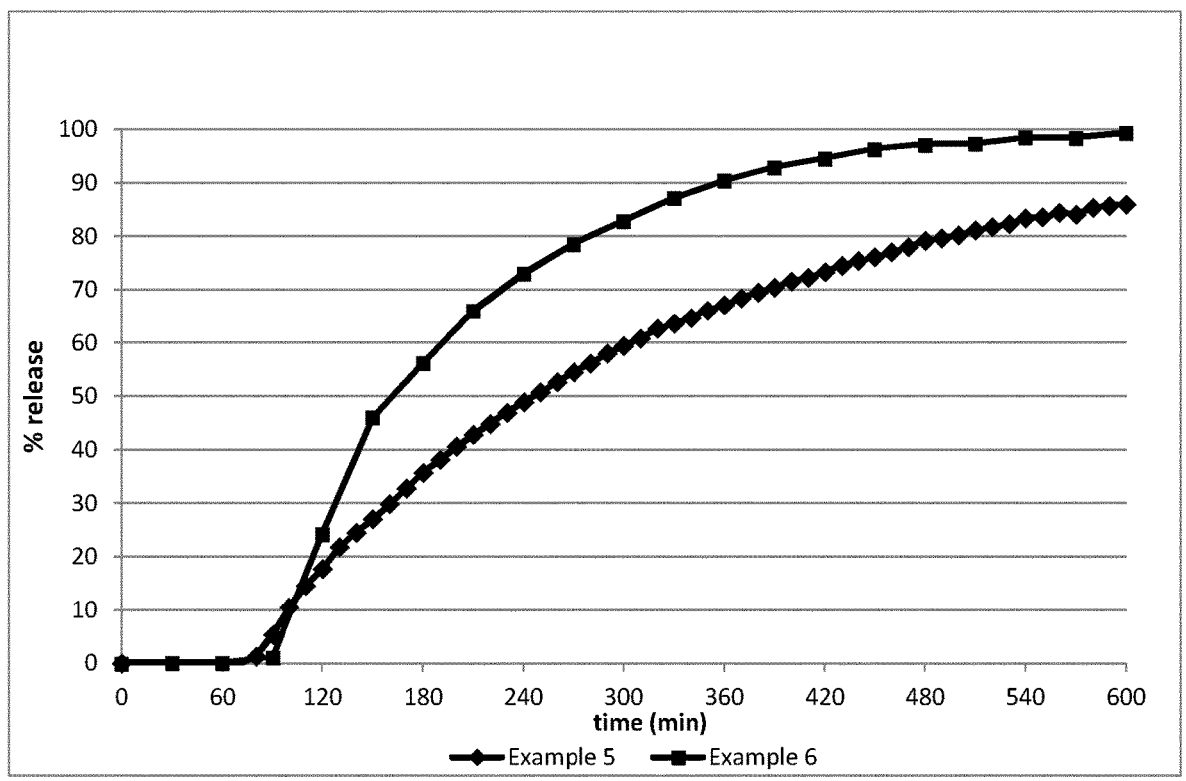
FIG. 5 shows a graph comparing drug release as a function of time from coated 5-ASA tablets according to Examples 5 and 6 when exposed to Kreb's buffer (pH 7.4) for 10 hours after pre-exposure to 0.1M HCl for 2 hours.

FIG. 1 is a graph depicting the correlation between compression force and tablet hardness for 1600 mg 5-ASA tablet cores produced using external lubrication according to Examples 2A-2G;

FIG. 2 is a graph depicting the correlation between tablet hardness and friability for 1600 mg 5-ASA tablet cores produced using external lubrication according to Examples 2A-2G;

FIG. 3 is a graph depicting the correlation between compression force and tablet hardness for 1600 mg 5-ASA tablet cores produced using internal lubrication according to Comparative Examples 3A-3H;

FIG. 4 is a graph depicting the correlation between tablet hardness and friability for 1600 mg 5-ASA tablet cores produced using internal lubrication according to Comparative Examples 3A-3H;

FIG. 5 is a graph comparing drug release as a function of time from coated 5-ASA tablets according to Examples 5 and 6 when exposed to Kreb's buffer (pH 7.4) for 10 hours after pre-exposure to 0.1M HCl for 2 hours.

MATERIALS

Eudragit® S 100 was purchased from Evonik GmbH, Darmstadt, Germany. Maize starch (Eurylon® 6 and Amylo N-400) was purchased from Roquette, Lestrem, France. Polysorbate 80 (Tween 80), butan-1-ol, triethylcitrate (TEC), ethanol 96%, potassium phosphate monobasic ($KH_2PO_4$), sodium diphosphate dibasic dihydrate ($Na_2HPO_4.2H_2O$), and sodium hydroxide were all purchased from Sigma-Aldrich, Buchs, Switzerland. Hydroxypropyl methylcellulose (HPMC, Pharmacoat® 603) was purchased from Shin-Etsu. Glyceryl monostearate (GMS) was purchased from Cognis. Iron oxide red and iron oxide yellow (Sicovit) were purchased from BASF. Microcrystalline cellulose (Avicel® pH 102) was purchased from FMS Biopolymer. Sodium starch glycolate (Explotab®) was purchased from JRS Pharma. Colloidal silicon dioxide (Aerosil® 200) was purchased from Degussa.

Preparation of Tablet Cores

Example 1—Preparation of 1200 mg 5-ASA Tablet Cores Using External Lubrication (Laboratory Scale)

Oblong shaped 1200 mg cores were prepared according to the following method. The amount of each component per tablet core is summarised in Table 1.

Mesalazine was added to a high shear mixer granulator and an aqueous composition of hydroxypropyl methylcellulose (Pharmacoat® 603) was slowly added over a period of 2 minutes at a mixing speed of 650 rpm. After mixing for an additional minute at 650 rpm, the deposit was removed from the mixing vessel wall and top and the remaining mixture mixed for an additional 3 minutes at 650 rpm with a chopper blade velocity of 600 rpm. The wet granules were passed through an oscillating granulator (2 mm sieve) before drying in a fluid bed dryer at an inlet air temperature of about 50° C. and a product temperature of 38° C. The dry granules were sieved through an oscillating granulator (1 mm sieve).

The dry granules were blended with for 10 minutes at 20 rpm with microcrystalline cellulose (Avicel® pH 102) and sodium starch glycolate (Explotab®) in a cube blender. Tableting was performed using a single punch excenter tablet press. Magnesium stearate was applied to the punches and dies of the tablet press with a brush.

Comparative Examples 1A to 1C—Preparation of 1200 mg 5-ASA Tablet Cores Using Internal Lubrication (Laboratory Scale)

Oblong shaped 1200 mg cores were prepared according to the following method. The amount of each component per tablet core is summarised in Table 1.

TABLE 1

| Component | Example 1 | Comparative Example 1A | Comparative Example 1B | Comparative Example 1C |
|---|---|---|---|---|
| | | Amount per tablet core (mg) | | |
| Mesalazine | 1200 | 1200 | 1200 | 1200 |
| Hypromellose | 24 | 24 | 24 | 24 |
| Microcrystalline cellulose | 136 | 129 | 127 | 125 |
| Sodium starch glycolate | 40 | 40 | 40 | 40 |
| Magnesium Stearate | 0* | 7 (0.5 wt %) | 9 (0.64 wt %) | 11 (0.79 wt %) |

*Tableting performed using external lubrication

Mesalazine was added to a high shear mixer granulator and an aqueous composition of hydroxypropyl methylcellulose (Pharmacoat® 603) was slowly added over a period of 2 minutes at a mixing speed of 650 rpm. After mixing for an additional minute at 650 rpm, the deposit was removed from the mixing vessel wall and top and the remaining mixture mixed for an additional 3 minutes at 650 rpm with a chopper blade velocity of 600 rpm. The wet granules were passed through an oscillating granulator (2 mm sieve) before drying in a fluid bed dryer at an inlet air temperature of about 50° C. and a product temperature of 38° C. The dry granules were sieved through an oscillating granulator (1 mm sieve).

The dry granules were blended for 10 minutes at 20 rpm with microcrystalline cellulose (Avicel® pH 102) and sodium starch glycolate (Explotab®) in a cube blender. Magnesium stearate was added and the resulting mixture was mixed for 3 minutes. Tableting was performed using a single punch excenter tablet press.

Examples 2A to 2G—Preparation of 1600 mg 5-ASA Tablet Cores Using External Lubrication (Pilot Scale)

Oblong shaped 1600 mg cores were prepared according to the following method. The amount of each component per tablet core and per batch of 20,000 tablet cores is summarised in Table 2.

TABLE 2

| Component | Amount per tablet core (mg) | Amount per batch of 20,000 tablet cores (g) |
|---|---|---|
| Mesalazine | 1600 | 32000 |
| Hypromellose P | 32 | 640 |
| Microcrystalline cellulose | 178 | 3560 |
| Sodium starch glycolate | 54 | 1080 |
| Magnesium stearate | 1 | 20 |
| Colloidal silicon dioxide | 2 | 40 |
| TOTAL MASS | 1867 | 37340 |

Mesalazine (8 kg) and an aqueous solution containing hydroxypropyl methylcellulose (160 g, Pharmacoat® 603) were granulated in a high speed mixer granulator. The wet granules were passed through a 9.4 mm sieve (Comil) before drying in a fluid bed dryer at an inlet air temperature of about 80° C. until the product temperature reached 42° C. The dry granules were sieved using a 1.6 mm grater sieve. The granulation was repeated for three further 8 kg batches of mesalazine.

The combined batches of dry granules were blended with microcrystalline cellulose (Avicel® pH 102) and sodium starch glycolate (Explotab®) in an 80 L drum for about 20 minutes at 28 rpm. Magnesium stearate and colloidal silicon dioxide (Aerosil® 200) were both individually pre-blended with about 500 g of the compression blend and passed through a 1 mm sieve before adding to the remaining compression blend. The mixture was blended for about 5 minutes at 28 rpm to form a final compression blend.

Compression of the final compression blend was performed using a Fette P1200 tableting machine combined with an external lubrication system (PKB). Magnesium stearate was sprayed onto the punches of the tableting machine at a dose of 400 g/h. The tableting machine was operated at a range of compression forces.

Comparative Examples 3A to 3H—Preparation of 1600 mg 5-ASA Tablet Cores Using Internal Lubrication (Pilot Scale)

Oblong shaped 1600 mg cores were prepared according to the following method. The amount of each component per tablet core and per batch of 20,000 tablet cores is summarised in Table 3.

TABLE 3

| Component | Amount per tablet core (mg) | Amount per batch of 20,000 tablet cores (g) |
|---|---|---|
| Mesalazine | 1600 | 32000 |
| Hypromellose | 32 | 640 |
| Microcrystalline cellulose | 167 | 3340 |
| Sodium starch glycolate | 54 | 1080 |
| Magnesium stearate | 12 | 240 |
| Colloidal silicon dioxide | 2 | 40 |
| TOTAL MASS | 1867 | 37340 |

Mesalazine (8 kg) and an aqueous solution of hydroxypropyl methylcellulose (160 g, Pharmacoat® 603) were granulated in a high shear mixer granulator. The wet granules were passed through a 9.4 mm sieve (Comil) before drying in a fluid bed dryer at an inlet air temperature of about 80° C. until the product temperature reached 42° C. The dry granules were sieved using a 1.6 mm grater sieve. The granulation was repeated for three further 8 kg batches of mesalazine.

The combined batches of dry granules were blended with microcrystalline cellulose (Avicel® pH 102) and sodium starch glycolate (Explotab®) in an 80 L drum for about 20 minutes at 28 rpm. Magnesium stearate and colloidal silicon dioxide (Aerosil® 200) were both individually pre-blended with about 500 g of the mixture of mesalazine granules, microcrystalline cellulose and sodium starch glycolate and passed through a 1 mm sieve before adding to the remainder of the mixture. The mixture was blended for about 5 minutes at 28 rpm to form a final compression blend.

Compression of the final compression blend was performed using a Fette P1200 tableting machine at a compression speed of 20,000 tablets/hour. The tableting machine was operated at a range of compression forces between 27 and 40 kN.

Examples 3 and 4—Scale Up of Method for Producing 1600 mg 5-ASA Tablet Cores Using External Lubrication Oblong shaped 1600 mg cores were prepared according to the following method. The amount of each component per tablet core is summarised in Table 4.

TABLE 4

|  | Example 3 | | Example 4 | |
| --- | --- | --- | --- | --- |
| Component | Amount per tablet core (mg) | Amount per 10,000 tablet cores (g) | Amount per tablet core (mg) | Amount per 80,000 tablet cores (g) |
| Mesalazine | 1600 | 16000 | 1600 | 128000 |
| Hypromellose | 32 | 320 | 32 | 2560 |
| Microcrystalline cellulose | 178 | 1780 | 178 | 14240 |
| Sodium starch glycolate | 54 | 540 | 54 | 4320 |
| Magnesium stearate | 1 | 10 | 1 | 80 |
| Colloidal silicon dioxide | 2 | 20 | 2 | 160 |
| TOTAL MASS | 1867 | 18670 | 1867 | 149360 |

A mixture of mesalazine (8 kg) and an aqueous solution of hydroxypropyl methylcellulose (160 g, Pharmacoat® 603) was granulated in a high shear mixer granulator. The wet granules were passed through a 9.4 mm sieve (Comil) before drying in a fluid bed dryer at an inlet air temperature of 80° C. and product temperature of about 42° C. for about 45 minutes. The dry granules were sieved using a 1.6 mm grater (Comil). Depending on the total batch size, multiple granulation batches were performed and combined before final blending.

The combined batches of dry granules were blended with microcrystalline cellulose (Avicel® pH 102) and sodium starch glycolate (Explotab®) in an 80 L bin blender at 28 rpm. Magnesium stearate and colloidal silicon dioxide (Aerosil® 200) were both individually pre-blended with about 500 g of the mixture of mesalazine granules, microcrystalline cellulose and sodium starch glycolate and passed through a 1 mm sieve before adding to the remainder of the mixture. The mixture was blended for about 5 minutes at 28 rpm to form a final compression blend Various properties were determined for the granules and the compression blend as summarised in Table 5 below.

TABLE 5

|  | Example 3 | Example 4 |
| --- | --- | --- |
| Granule | | |
| LOD (%) | 0.33 | 0.26 |
| Flow (s) | 4.2 | 8 |
| Bulk density (g/l) | 610 | 550 |
| Tapped density (g/l) | 775 | 660 |
| Angle of repose (°) | 36.0 | 28.9 |
| Compression blend | | |
| LOD (%) | 1.20 | 0.97 |
| Flow (s) | 4.0 | 4.0 |
| Bulk density (g/l) | 650 | 625 |
| Tapped density (g/l) | 787 | 750 |
| Angle of repose (°) | 32 | 26 |

Compression of the final compression blend was performed using a Fette P1200 tableting machine combined with an external lubrication system (PKB) at a compression speed of 20,000 tablets/hour. Magnesium stearate was sprayed onto the punches and dies of the tableting machine at a dose of 400 g/h.

Drug Release Test #1—Dissolution in 0.05 M Phosphate Buffer at pH 7.2

In vitro dissolution studies were performed on a USP type II apparatus using a 0.05 M phosphate buffer at pH 7.2. A paddle rotation speed of 50 rpm was used for the dissolution period (30 minutes) following by a rotation speed 100 rpm for further 30 minutes to confirm recovery of drug content in the dosage form.

Results

The physical properties of the 1200 mg tablet cores produced in Example 1 and Comparative Examples 1A to 1C are summarised in Table 6 below. The tablet cores according to Example 1 demonstrate superior hardness and friability when compared with Comparative Examples 1A to 1C. This data demonstrates that the use of external lubrication produces tablet cores having superior physical properties to those produced using only an internal lubricant when produced on a laboratory scale.

TABLE 6

|  | Example 1 | Comparative Example 1A | Comparative Example 1B | Comparative Example 1C |
| --- | --- | --- | --- | --- |
| Average tablet core thickness, (mm) | 6.92 | 6.84 | 6.92 | 6.88 |
| Average tablet core hardness, (N) | 307.9 | 258.6 | 260.6 | 244.4 |
| Hardness range (N) | 293-325 | 248-282 | 252-270 | 210-256 |
| Tablet friability (%) | 0.042 | 0.10 | 0.064 | 0.178 |
| Disintegration time, range (min) | 3.35-4.42 | 7.09-7.49 | 6.39-7.51 | 7.26-7.54 |
| Drug release in phosphate buffer @ pH 7.2 (%) | | | | |
| 5 minutes | 43 | 20 | 29 | 23 |
| 10 minutes | 57 | 33 | 48 | 37 |
| 15 minutes | 67 | 42 | 61 | 50 |
| 20 minutes | 73 | 51 | 71 | 59 |
| 25 minutes | 78 | 55 | 75 | 64 |
| 30 minutes | 79 | 59 | 79 | 69 |

The drug release profiles for the tablets cores of Example 1 and Comparative Examples 1A to 1C after exposure to phosphate buffer at 0.05 M (drug release test #1) are also summarised in Table 6. The data clearly demonstrate that tablet cores according to the present invention produced using external lubrication (Example 1) have a significantly shorter disintegration time and a faster dissolution rate when compared to those prepared using internal lubrication (Comparative Examples 1A to 1C).

Pilot plant scale production of 1600 mg tablet cores using external lubrication was also possible across a wide range of compression forces (Table 7). The low variability of the tablet mass with increasing compression force indicates that the compression blend has acceptable flow properties. No capping is observed for any of the tablets tested. A significant reduction in ejection force is observed when both the dies and the punches of the tableting machine are lubricated (Example 2G).

TABLE 7

| | Example No. | | | | | | |
|---|---|---|---|---|---|---|---|
| | 2A | 2B | 2C | 2D | 2E | 2F | 2G |
| Compression conditions | | | | | | | |
| Compression Force (kN) | 15 | 21.2 | 25.8 | 30.8 | 35.7 | 39.7 | 29.3 |
| Ejection Force (N) | 88** | 120** | 148** | 196** | 388** | 498** | 145*** |
| Testing on the Tablet Core | | | | | | | |
| Hardness (N) | 155 | 187 | 218 | 254 | 274 | 290 | 258 |
| Friability (%) | 0.54 | 0.26 | 0.12 | 0.063 | 0.055 | 0.03 | 0.058 |
| Tablet thickness (mm) | 9.16 | 8.92 | 8.77 | 8.67 | 8.59 | 8.56 | 8.65 |
| Tablet mass (mg) | 1865 | 1864 | 1867 | 1866 | 1865 | 1870 | 1862 |

**only punches were lubricated
***dies and punches were lubricated

A correlation between increasing compression force and tablet hardness is observed (FIG. 1) as well as a correlation between tablet hardness and friability (FIG. 2).

By comparison, tablet cores compressed using only internal lubrication have a tendency for capping during friability testing (Table 8, Comparative Examples 3B and 3D-3F). Sticking of the tablets to the punches of the tableting machine is also observed and the high ejection force values indicate that the level of lubricant in the compression blend is insufficient (Table 8). However, as demonstrated in Comparative Examples 1A to 1B, a further increase in the amount of internal lubricant has a negative effect on the tablet quality.

TABLE 8

| | Comparative Example No. | | | | | | | |
|---|---|---|---|---|---|---|---|---|
| | 3A | 3B | 3C | 3D | 3E | 3F | 3G | 3H |
| Compression conditions | | | | | | | | |
| Compression Force (kN) | 26.9 | 33.4 | 35.5 | 35.9 | 39.3 | 39.6 | 33.4 | 33.6 |
| Ejection Force (N) | 487 | 530 | 537 | 566 | 593 | 576 | n.p.** | 520 |
| Testing on the tablet core | | | | | | | | |
| Hardness (N) | 226 | 258 | 251 | 255 | 236 | 273 | 252 | 257 |
| Friability (%) | 0.54 | 0.127+ | 0.22 | 0.37+ | 0.06+ | 0.083+ | 0.21 | 0.174 |
| Disintegration time (min.) | 5.3 | 7.75 | 10.75 | 10 | 9.22 | 10.83 | 7.25 | 7.63 |
| Tablet thickness (mm) | 8.77 | 8.65 | 8.59 | 8.63 | 8.55 | 8.55 | 8.63 | 8.61 |
| Tablet mass (mg) | 1872 | 1869 | 1868 | 1874 | 1870 | 1869 | 1868 | 1864 |

+capping occurred during friability test
**n.p. = not performed

Moreover, with the use of only internal lubrication, compression of the compression blends is only possible across a narrow compression force range and no correlation is observed between compression force and hardness or between hardness and friability (see FIG. 3 and FIG. 4). It is believed that the presence of the lubricant in the compression blend (internal lubrication) may hinder the compression of the blend, since an increase in compression force does not result in an increase in tablet hardness.

Scale up of the external lubrication process for the preparation of 1600 mg tablet cores was successful, and delivered tablet cores having acceptable strength as exemplified by low friability and high hardness (Table 9). The tablet cores according to the present invention also demonstrate rapid disintegration time.

TABLE 9

| | Example 3 | Example 4 |
|---|---|---|
| Mass (mg) | 1864-1872 | 1863-1868 |
| Hardness (N) | 262-272 | 263-269 |
| Friability (%) | 0.1 | 0.14-0.23 |
| Disintegration time (min) | 4.5-5 | 4.9-5.3 |
| Thickness (mm) | 8.7 | 8.65-8.66 |
| Yield (kg) | 14.374 | 142.4 |
| Total Number of tablets | 7709 | 76325 |

Preparation of Coated Tablet Cores

Examples 5 and 6—Coating of 1200 mg and 1600 mg 5-ASA Tablet Cores

Tablet cores containing 1200 mg and 1600 mg mesalazine (5-ASA) were provided.

The tablet cores of Example 5 (1200 mg 5-ASA) were coated with an isolation layer of hypromellose (hydroxypropyl methylcellulose, HPMC) at 3 mg/cm$^2$ with 20% macrogol 6000 and an outer layer of 70% methacrylic acid-methyl methacrylate copolymer, ratio 1:2 (Eudragit® S 100) and 30% high amylose starch at 5 mg/cm$^2$.

The tablet cores of Example 6 (1600 mg 5-ASA) were coated with the same isolation layer as for Example 5, an inner layer of methacrylic acid-methyl methacrylate copolymer, ratio 1:2 (Eudragit® S 100) and 1% potassium dihydrogen phosphate neutralized to pH 8 at 5 mg/cm$^2$, and an outer layer of methacrylic acid-methyl methacrylate copolymer, ratio 1:2 (Eudragit® S 100) at 5 mg/cm$^2$.

Isolation Layer

The isolation layer was applied by spray coating in the following amounts:

TABLE 10

| Component | mg/cm$^2$ |
|---|---|
| HPMC | 3 |
| Macrogol 6000 | 0.6 |

The isolation layer coating preparation was sprayed on to the tablets cores using a pan coater until the coating amount of HPMC reached 3 mg/cm$^2$ to produce intermediate (isolation layer) coated cores.

The spray coating parameters were as follows:

TABLE 11

| Pan rotation speed (rpm) | 10 |
|---|---|
| Nozzle diameter (mm) | 1.0 |
| Number of spray guns | 1 |
| Spray rate (g/min) | 3.2 |
| Angle of spray gun on tablet bed (°) | 90 |
| Atomisation air pressure (bar) | 0.4 |
| Pattern air pressure (bar) | 0.5 |
| Air flow (m$^3$/h) | 30 |
| Outlet air temperature (° C.) | 41.3-43.5 |

Inner Layer (of Example 6)

The tablet cores coated with an isolation layer were then coated with an inner layer coating of partially neutralised methacrylic acid-methyl methacrylate copolymer, ratio 1:2 (Eudragit® S 100), and 1% KH$_2$PO$_4$ buffer agent.

The inner layer was applied by spray coating in the in the following amounts:

TABLE 12

| Component | mg/cm$^2$ |
|---|---|
| Eudragit® S 100 | 5 |
| KH$_2$PO$_4$ | 0.05 |
| Triethyl citrate | 3.5 |
| Glyceryl monostearate | 0.5 |
| Polysorbate 80 | 0.2 |
| 1M NaOH | As required to reach pH 8 |

The pH was adjusted using 1M NaOH until pH 8 was obtained. KH$_2$PO$_4$ was dissolved in distilled water, followed by dispersion of the partially neutralized Eudragit® S 100.

The inner layer coating preparation was sprayed on to the isolation layer coated cores using a pan coater until the coating amount of Eudragit® S 100 reached 5 mg/cm$^2$, to produce intermediate (inner layer) coated cores.

The spray coating parameters were as follows:

TABLE 13

| Pan rotation speed (rpm) | 10-12 |
|---|---|
| Nozzle diameter (mm) | 1.0 |
| Number of spray guns | 1 |
| Spray rate (g/min) | 3.25 |
| Angle of spray gun on tablet bed (°) | 90 |
| Atomisation air pressure (bar) | 0.4 |
| Pattern air pressure (bar) | 0.5 |
| Air flow (m$^3$/h) | 40 |
| Outlet air temperature (° C.) | 40.3-42.7 |

Outer Layer (of Example 5)

The isolation layer coated tablet cores were coated with an outer layer coating formed of 70% methacrylic acid-methyl methacrylate copolymer, 1:2 (Eudragit® S 100) and 30% high amylose starch.

The outer layer coating was applied from a mixture of an aqueous starch dispersion and an ethanolic Eudragit® S 100 solution in the following amounts:

TABLE 14

| | Example 5 | |
|---|---|---|
| Component | mg/cm$^2$ | mg/tab |
| | Starch dispersion | |
| Eurylon® 6 | 3.18 | 28.7 |
| | Eudragit® S 100 suspension | |
| Eudragit® S 100 | 6.5 | 37.31 |
| Triethyl citrate | 1.86 | 10.66 |
| Glyceryl monostearate | 0.46 | 2.67 |
| Polysorbate 80 | 0.19 | 1.07 |
| Iron oxide red | 0.86 | 4.92 |
| Iron oxide yellow | 0.15 | 0.85 |

The aqueous starch dispersion was prepared by dispersing high amylose maize starch, (Eurylon® 6) into butan-1-ol, followed by water, under magnetic stirring. The ratio of maize starch:butan-1-ol:water was 1:1:12.5. The resulting dispersion was heated to boiling and then cooled under stirring overnight.

The Eudragit® S 100 solution was prepared by dispersing Eudragit® S 100 in 96% ethanol under high speed stirring. The final solution contained approximately 6% polymer solids.

The starch dispersion was added dropwise to the Eudragit® S 100 solution under stirring to obtain a ratio of Eudragit® S 100:starch of 70:30. The mixture was stirred for 1 hour and 40% TEC (based on Eudragit® S 100 polymer weight) and 10% GMS (based on Eudragit® S 100 polymer weight) were added and mixed for further 30 minutes. A suspension of 13.16% iron oxide red (based on Eudragit® S 100 polymer weight) and 2.23% iron oxide yellow (based on Eudragit® S 100 polymer weight) was added and the mixture was stirred for a further 10 minutes.

The GMS was added in the form of an emulsion prepared at a concentration of 5% w/w. Polysorbate 80 (Tween, 40% based on GMS weight) was dissolved in distilled water followed by dispersion of the GMS. The dispersion was heated at 75° C. for 15 minutes under strong magnetic stirring in order to form an emulsion. The emulsion was cooled at room temperature under stirring.

The pigment suspension was formed by suspending red and yellow iron oxide pigments in 96% ethanol for 10 minutes under homogenization.

The final outer layer coating preparation was sprayed on to the isolation layer coated tablet cores until the coating amount of Eudragit® S 100 reached 5 mg/cm².

Outer Layer (Example 6)

The tablet cores coated with an isolation layer and an inner layer were coated with an outer layer coating formed of methacrylic acid-methyl methacrylate copolymer, 1:2 (Eudragit® S 100).

The outer layer coating was applied from an ethanolic Eudragit® S 100 solution in the following amounts:

TABLE 15

| Example 6 | | |
|---|---|---|
| Component | mg/cm² | mg/tab |
| Eudragit ® S 100 | 5 | 34.55 |
| Triethyl citrate | 1 | 13.82 |
| Glyceryl monostearate | 0.25 | 3.46 |
| Polysorbate 80 | 0.10 | 1.38 |
| Iron oxide red | 0.66 | 4.55 |
| Iron oxide yellow | 0.11 | 0.79 |

The outer coating was prepared by dispersing Eudragit® S 100 in 96% ethanol under high speed stirring following by the addition of TEC and a GMS emulsion (prepared as in Example 5). Lastly, a suspension of iron oxide red and iron oxide yellow (prepared as in Example 5) was added to the mixture and the mixture stirred for further 10 minutes.

The final outer layer coating preparation was sprayed on to the isolation layer and inner layer coated tablet cores until the coating amount of Eudragit® S 100 reached 5 mg/cm².

The spray coating parameters for applying the outer layer coatings were as follows:

TABLE 16

|  | Example 5 | Example 6 |
|---|---|---|
| Pan rotation speed (rpm) | 16 | 12-14 |
| Nozzle diameter (mm) | 1.0 | 1 |
| Number of spray guns | 1 | 1 |
| Angle of spray gun on tablet bed (°) | 90 | 90 |
| Atomisation air pressure (bar) | 0.4 | 0.4 |
| Pattern air pressure (bar) | 0.5 | 0.5 |
| Air flow (m³/h) | 40 | 40 |
| Outlet air temperature (° C.) | 40-41 | 33.1-35.8 |

Drug Release Test #2—Simulated Fasted State then Dissolution in Hanks Buffer at pH 6.8

In vitro dissolution studies were performed on a USP type II apparatus using a paddle speed of 50 rpm and a media temperature of 37±0.5° C. To simulate the "fasted" state, tablets were first tested in 0.1 M HCl for 2 hours followed 10 hours in Hanks buffer (pH 6.8).

The pH of the buffer was stabilized at 6.8±0.05 by continuously sparging with 5% $CO_2$/95% $O_2$. Absorbance measurements were taken at 5 minute intervals, with an absorbance wavelength of 301 nm in HCl and 330 nm in Hanks buffer pH 6.8.

Drug Release Test #3—Simulated Fasted State then Dissolution in Krebs Buffer at pH 7.4

In vitro dissolution studies were performed on a USP type II apparatus using a paddle speed of 50 rpm and a media temperature of 37±0.5° C.

To simulate the "fasted" state, tablets were first tested in 0.1 M HCl for 2 hours followed by 10 hours in Krebs buffer (pH 7.4).

Results

It was possible to coat the 1200 mg and 1600 mg tablet cores of the present invention with known delayed release coatings. The results demonstrate that the coated tablets prepared according to the present invention were resistant to simulated gastric fluid and show rapid drug release upon exposure to simulated conditions of the ileo-colonic region.

The 1200 mg coated tablets of Examples 5 and the 1600 mg coated tablets of Example 6 were tested in vitro for drug release in pH 6.8 Hanks buffer after exposure to simulated gastric conditions. In both cases the coated tablets were gastric resistant and drug release was below 5% when exposed to simulated conditions of the proximal small intestine (Hanks buffer at pH 6.8). This demonstrates robustness of the coated tablets during transit through the small intestine.

However, it should be noted that, upon exposure to pH 7.4 (drug release test #3) to simulate the conditions in the ileo-colonic region, rapid drug release was observed for both the 1200 mg and 1600 mg coated tablets of the present invention (FIG. 5).

It will be appreciated that the invention is not restricted to the details described above with reference to the preferred embodiments, but that numerous modifications and variations can be made without departing from the scope of the invention.

The invention claimed is:

1. A method of producing a coatable core for a modified release drug formulation for oral administration, the coatable core having a high drug load of at least 70 wt % based on a total weight of the coatable core, wherein the drug is present in the core in an amount of more than 1200 mg, the method comprising:
   granulating a composition comprising a drug and at least one binder to form granules;
   blending the granules with a pharmacologically acceptable disintegrant and optionally, one or more additional pharmacologically acceptable excipients, to form a compression blend, wherein the disintegrant is present in an amount from about 0.5 wt % to about 5 wt %, based on the total weight of the coatable core; and
   compressing the compression blend using an external lubrication compression method, to form a coatable core.

2. The method as claimed in claim 1, wherein said composition further comprises at least one granulation liquid, and
   wherein said method further comprises drying said granules to form dry granules.

3. The method as claimed in claim 2, wherein said granulation liquid is water.

4. The method as claimed in claim 1, wherein the coatable core has a drug load of from about 85 wt % to about 95 wt %, based on the total weight of the coatable core.

5. The method as claimed in claim 1, wherein the at least one binder is present in an amount of about 3 wt % or less, based on the total weight of the coatable core.

6. The method as claimed in claim 1, wherein the disintegrant is present in an amount of about 0.5 wt % to about 3 wt %, based on the total weight of the coatable core.

7. The method as claimed in claim 1, wherein the one or more additional pharmacologically acceptable excipient is present and comprises a lubricant.

8. The method as claimed in claim 7, wherein the lubricant is present, and is present in an effective amount to provide lubrication and about 0.5 wt % or less, based on the total weight of the coatable core.

9. The method as claimed in claim 1, wherein the drug is present in the core in an amount from about 1550 mg to about 1650 mg.

10. The method as claimed in claim 1, wherein the drug is present in the core in an amount selected from the group consisting of about 1200 mg, about 1500 mg, and about 1600 mg.

11. The method as claimed in claim 1, wherein the granules have a bulk density of at least about 540 g/l.

12. The method as claimed in claim 1, wherein the compression blend has a bulk density of at least about 600 g/l.

* * * * *